(12) United States Patent
Bedoya et al.

(10) Patent No.: US 12,193,659 B2
(45) Date of Patent: Jan. 14, 2025

(54) VAGINAL CUFF CLOSURE LAPAROSCOPIC SUTURE PASSER

(71) Applicant: HOLOGIC, INC., Marlborough, MA (US)

(72) Inventors: Marco Bedoya, Marlborough, MA (US); Catherine Withers, Marlborough, MA (US)

(73) Assignee: Hologic, Inc., Marlborough, MA (US)

( * ) Notice: Subject to any disclaimer, the term of this patent is extended or adjusted under 35 U.S.C. 154(b) by 183 days.

(21) Appl. No.: 17/194,206

(22) Filed: Mar. 5, 2021

(65) Prior Publication Data

US 2021/0275167 A1    Sep. 9, 2021

Related U.S. Application Data

(60) Provisional application No. 62/992,017, filed on Mar. 19, 2020, provisional application No. 62/986,257, filed on Mar. 6, 2020.

(51) Int. Cl.
| | |
|---|---|
| *A61B 17/04* | (2006.01) |
| *A61B 17/00* | (2006.01) |
| *A61B 17/06* | (2006.01) |
| *A61B 17/42* | (2006.01) |

(52) U.S. Cl.
CPC .... *A61B 17/0469* (2013.01); *A61B 17/06066* (2013.01); *A61B 17/42* (2013.01); *A61B 2017/00438* (2013.01); *A61B 2017/06085* (2013.01); *A61B 2017/061* (2013.01)

(58) Field of Classification Search
CPC .......... A61B 17/0469; A61B 17/06066; A61B 17/42; A61B 2017/00438; A61B 2017/06085; A61B 2017/061; A61B 2017/00353; A61B 17/0483; A61B 17/0482; A61B 2017/06052; A61B 2017/2926; A61B 2017/00424
See application file for complete search history.

(56) References Cited

U.S. PATENT DOCUMENTS

| | | | | |
|---|---|---|---|---|
| 2,814,296 A | * | 11/1957 | Samuel | A61B 17/06 427/2.28 |
| 5,383,877 A | * | 1/1995 | Clarke | A61B 17/0469 606/139 |
| 5,797,927 A | * | 8/1998 | Yoon | A61B 17/0469 606/139 |

(Continued)

*Primary Examiner* — Tan-Uyen T Ho
*Assistant Examiner* — David P Stein
(74) *Attorney, Agent, or Firm* — Vista IP Law Group, LLP

(57) ABSTRACT

A laparoscopic suture passer comprises an elongated shaft, and a jaw assembly coupled to a distal end of the elongated shaft. The jaw assembly comprises first and second jaw members hingedly associated with each other. The jaw members are configured for being alternately displaced relative to each other between an open position and a closed position. The laparoscopic suture passer further comprises a hollow needle comprising a slotted bore extending along the entire length thereof. The hollow needle has a blunt end and a sharp end opposite the blunt end. The blunt end of the hollow needle is hingedly coupled to the first jaw member for being alternately hinged between a retracted position, wherein the hollow needle is stowed in the first jaw member, and a deployed position, wherein the hollow needle extends away from the first jaw member.

6 Claims, 38 Drawing Sheets

(56) References Cited

U.S. PATENT DOCUMENTS

| | | | | |
|---|---|---|---|---|
| 5,895,393 A | * | 4/1999 | Pagedas | ............ A61B 17/0483 |
| | | | | 606/139 |
| 10,405,851 B2 | * | 9/2019 | Gorski | ............ A61B 17/06166 |
| 2009/0312773 A1 | * | 12/2009 | Cabrera | ............ A61B 17/0469 |
| | | | | 606/144 |

* cited by examiner

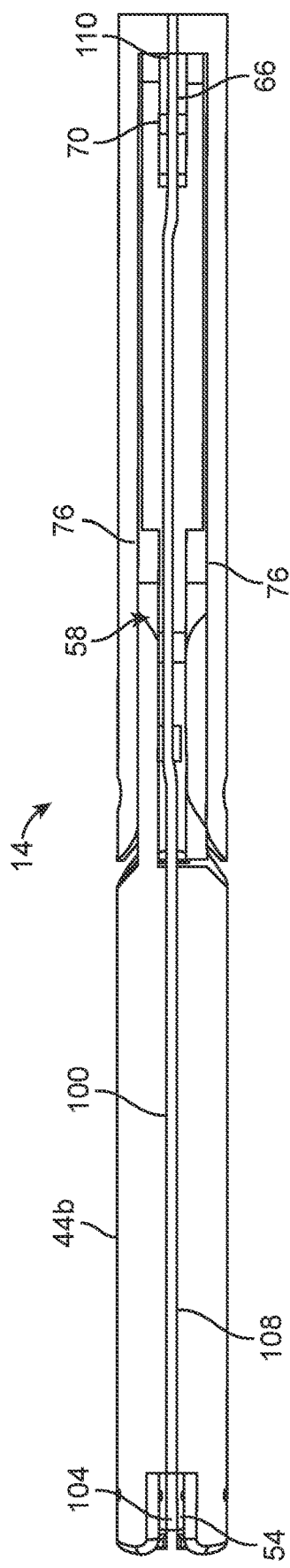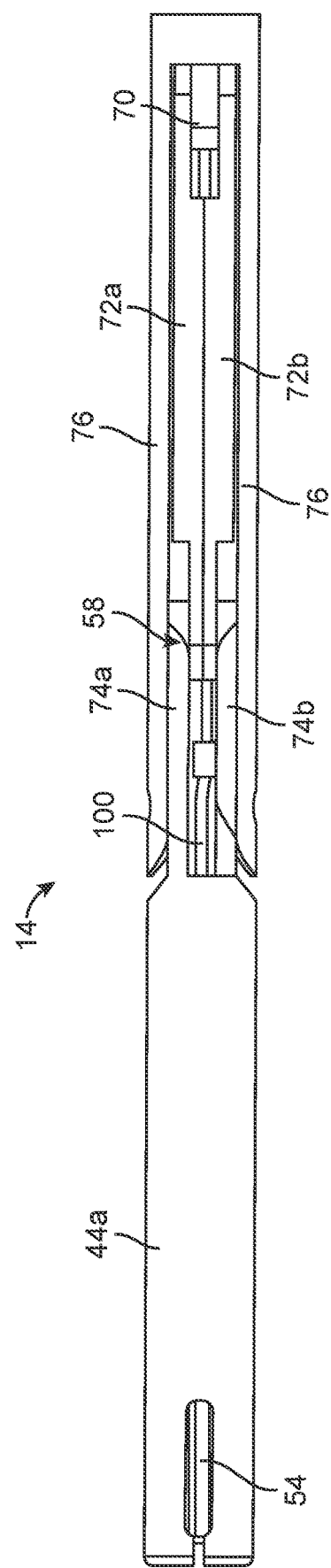
FIG. 8
FIG. 9

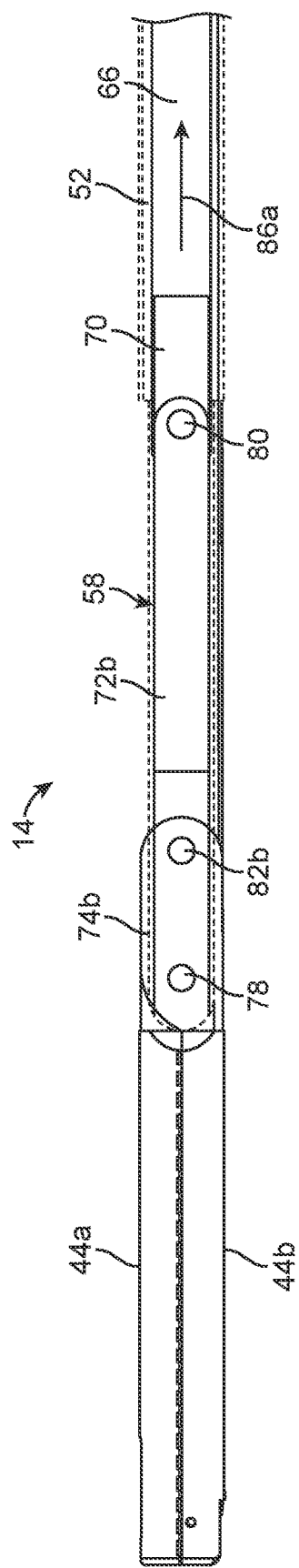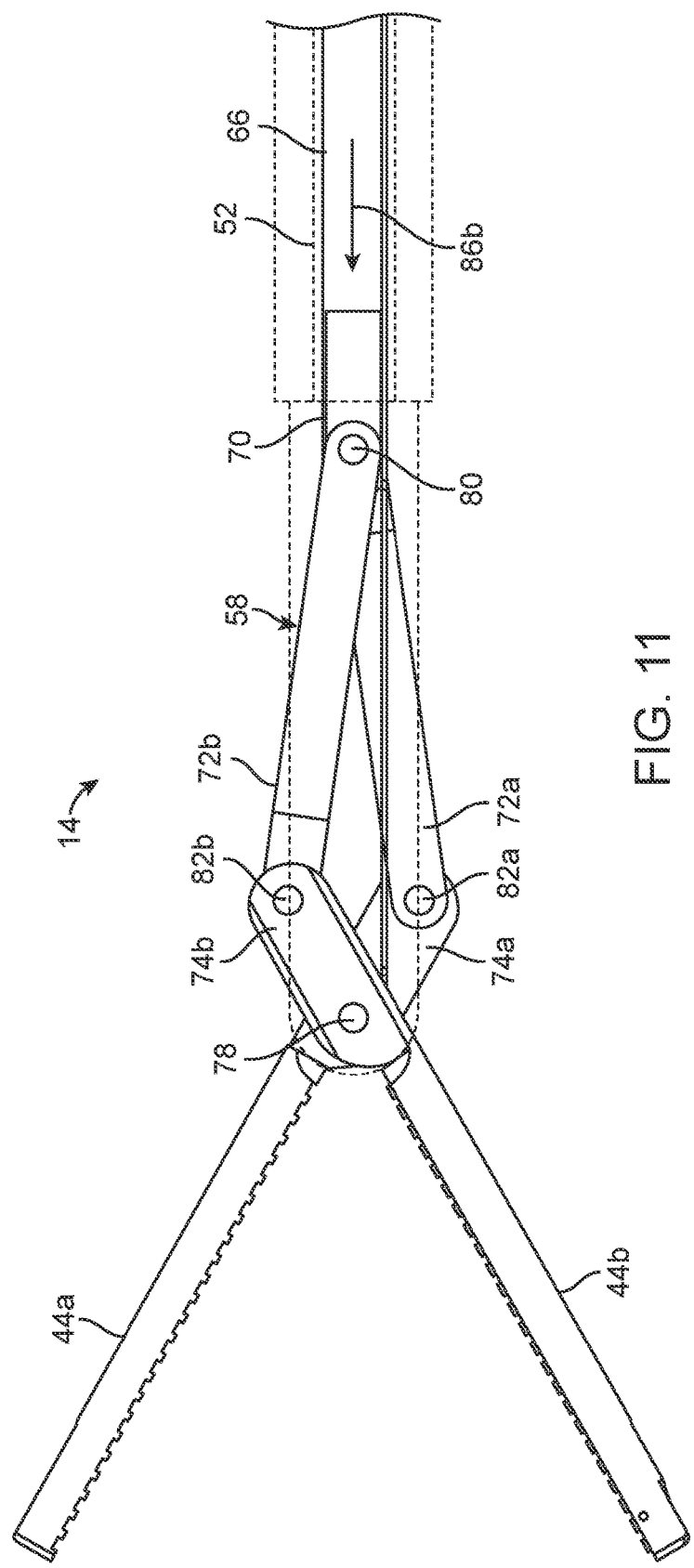

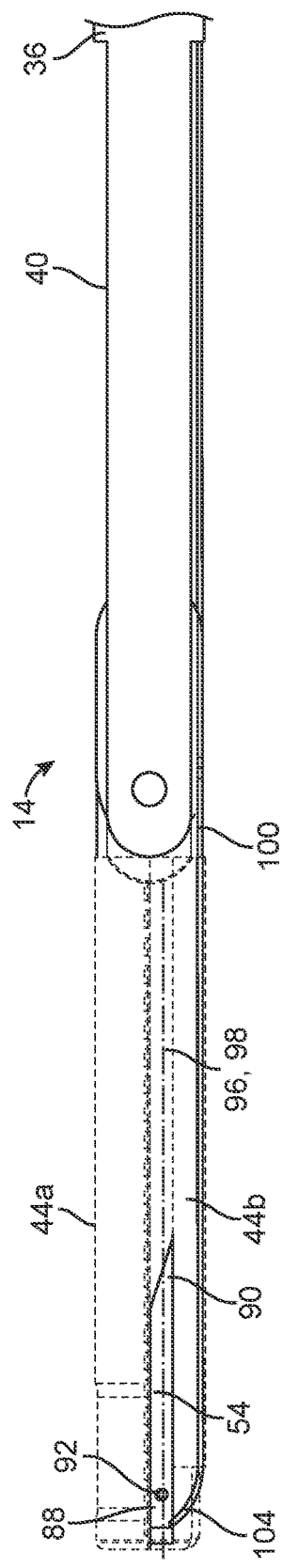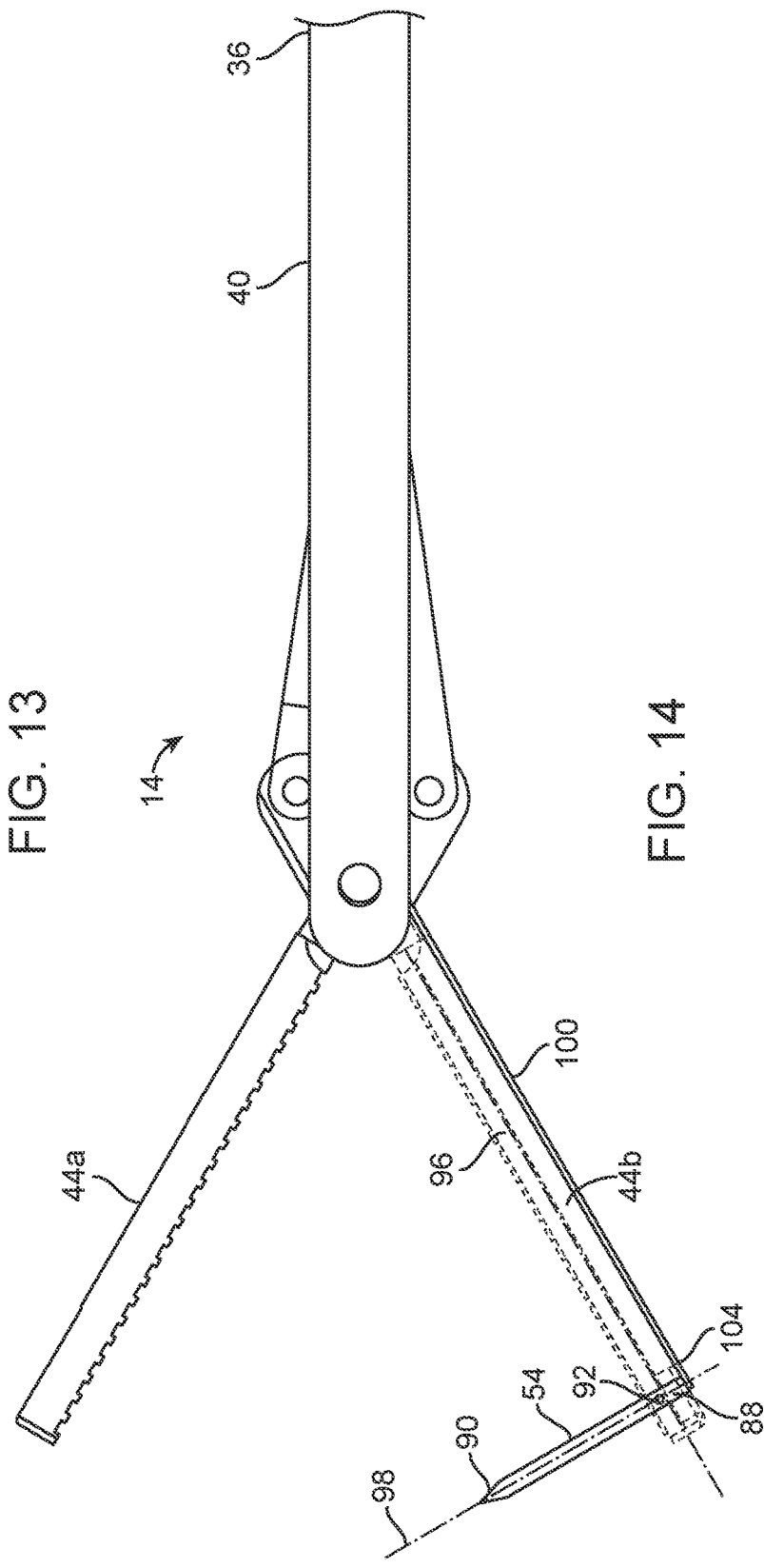
FIG. 13
FIG. 14

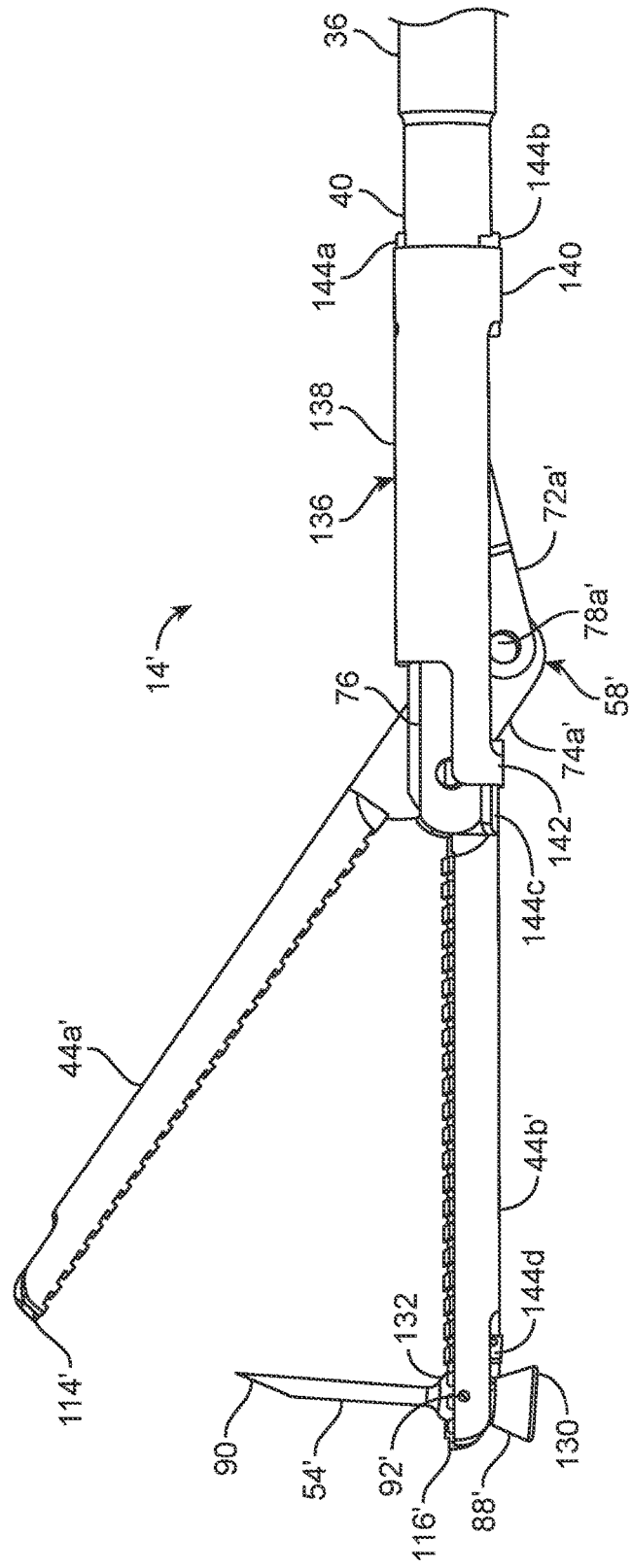
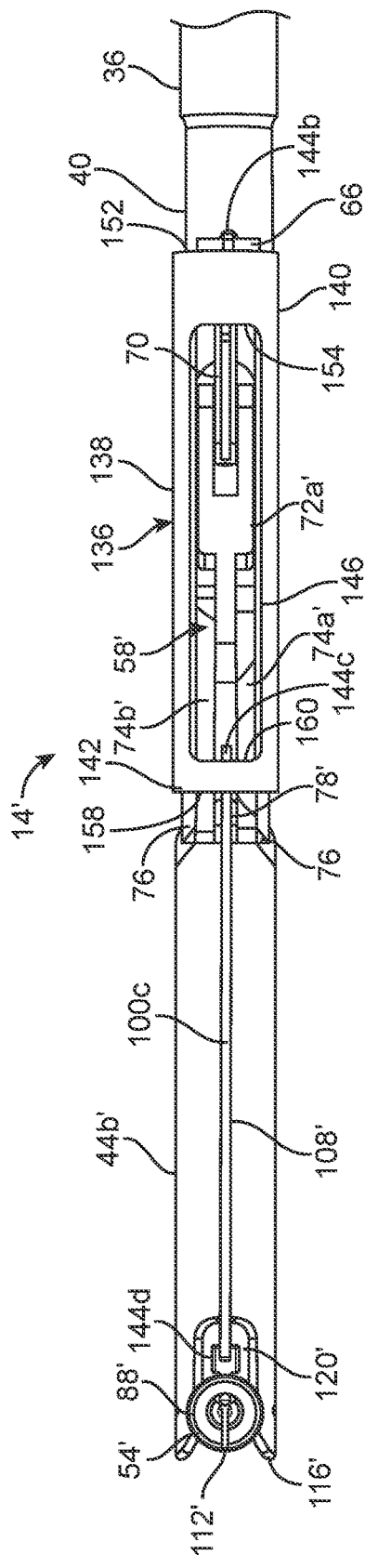
FIG. 19
FIG. 20

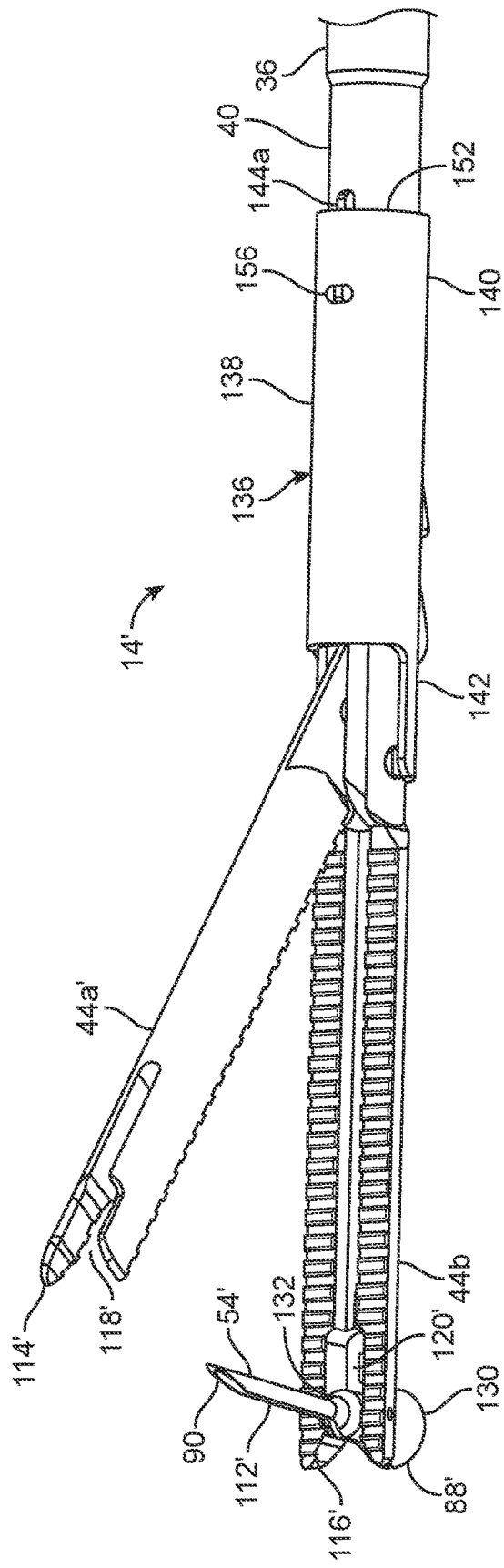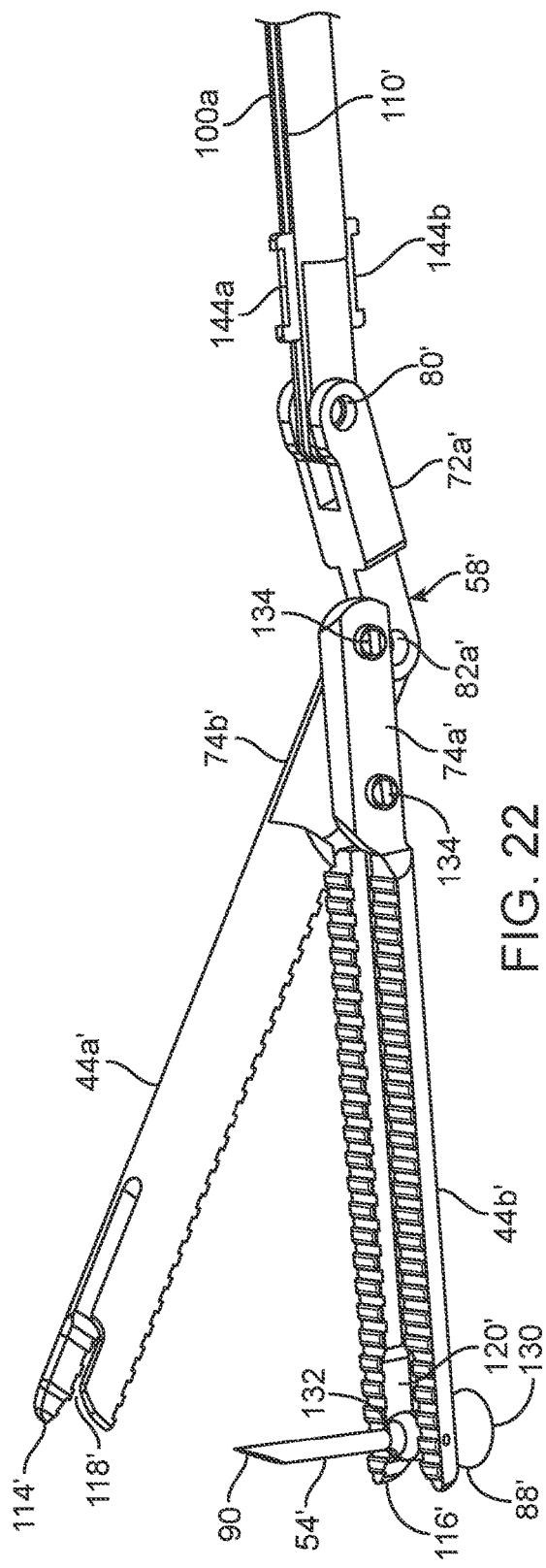

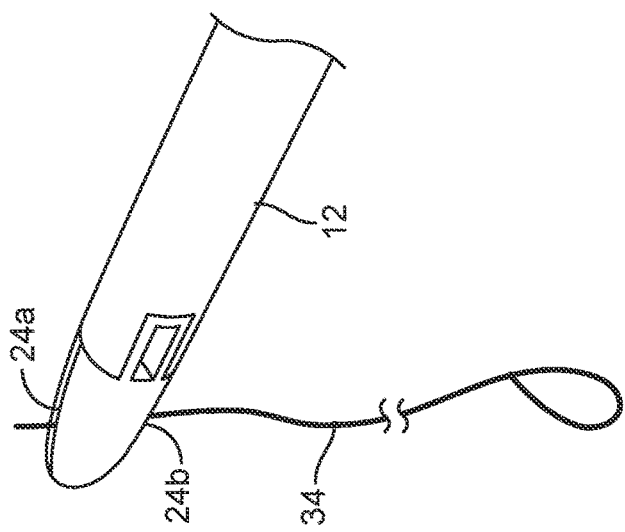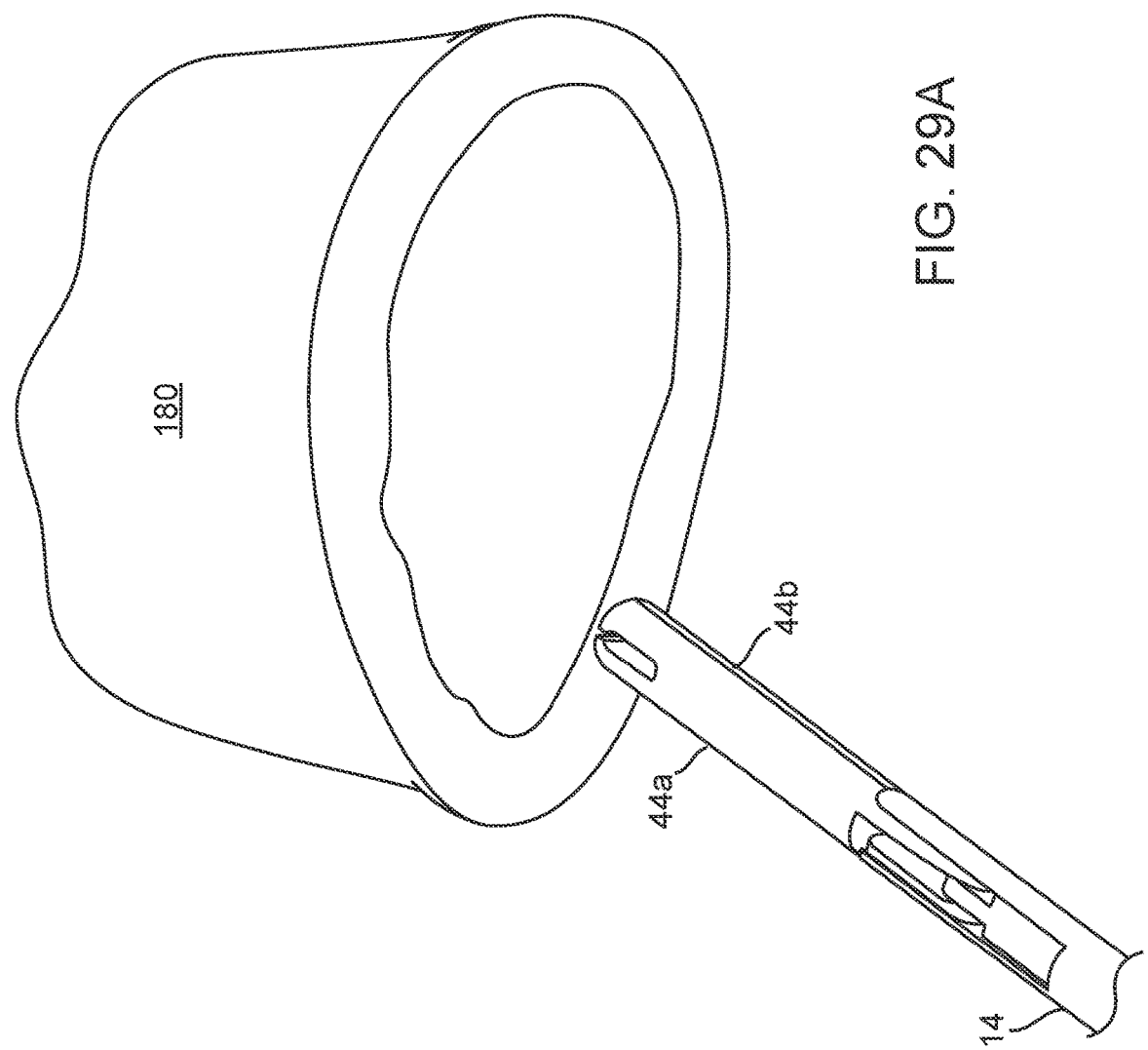
FIG. 29A

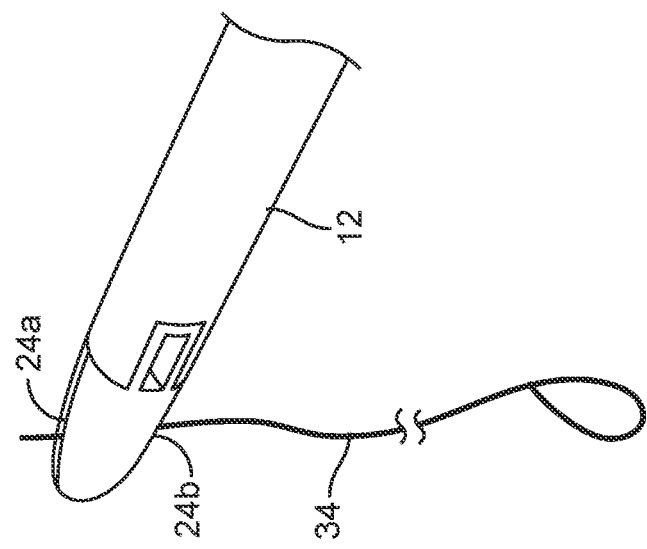
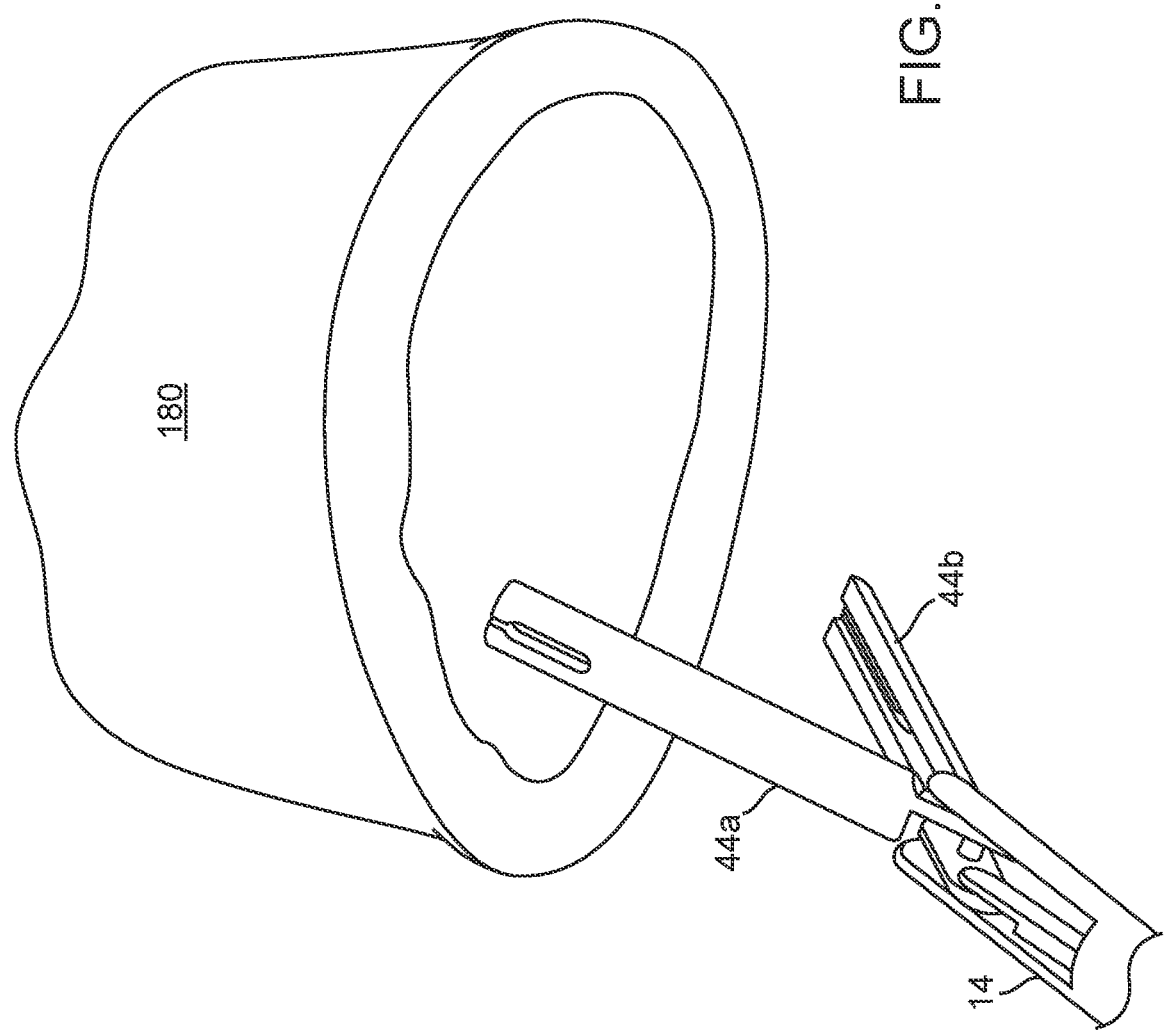
FIG. 29B

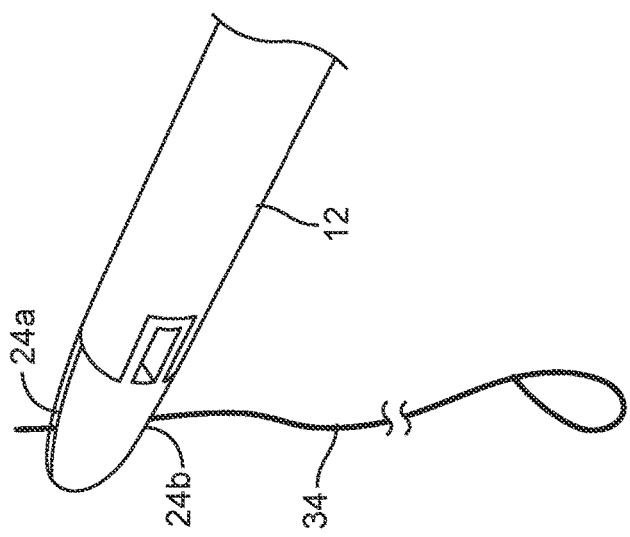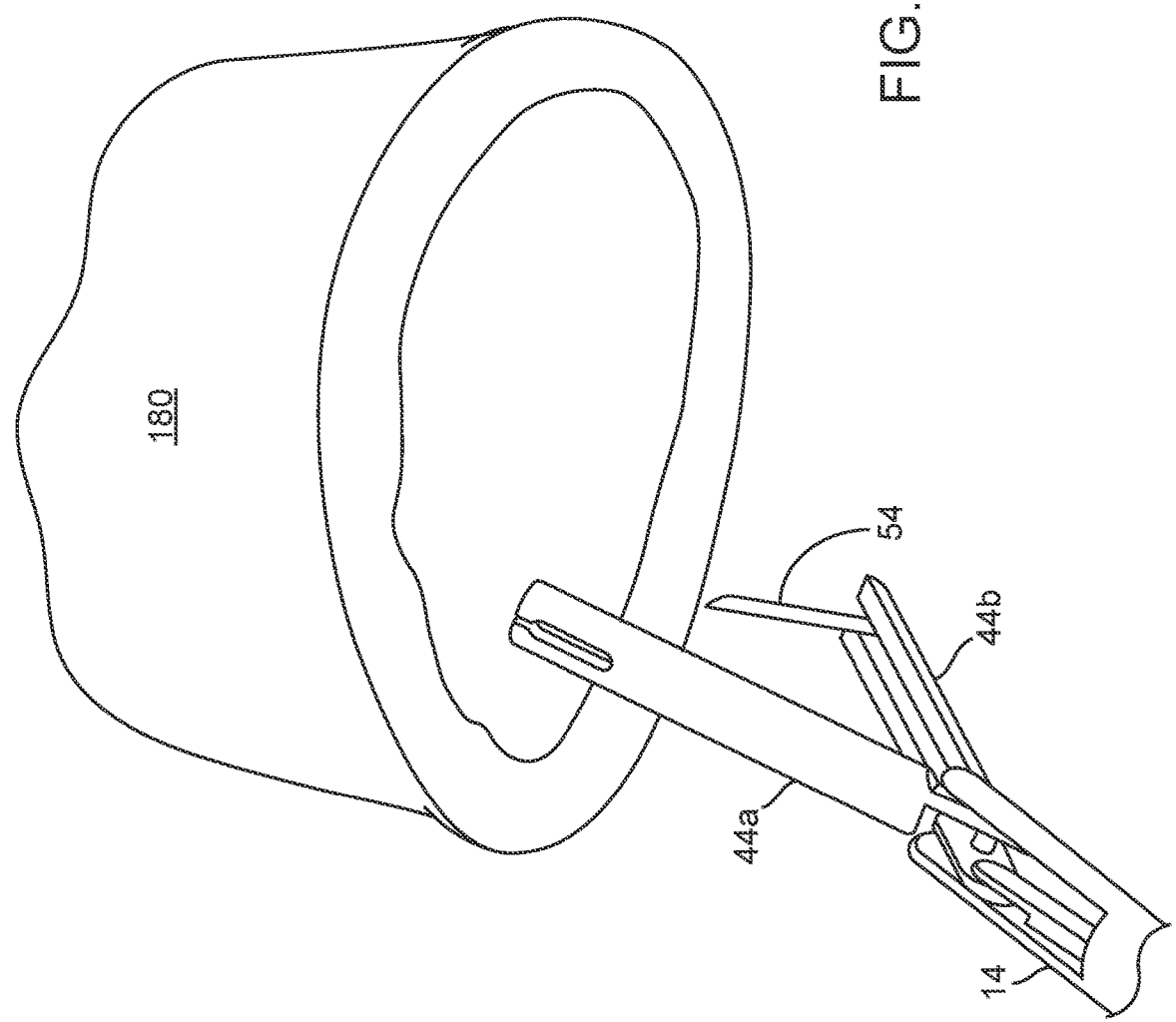
FIG. 29C

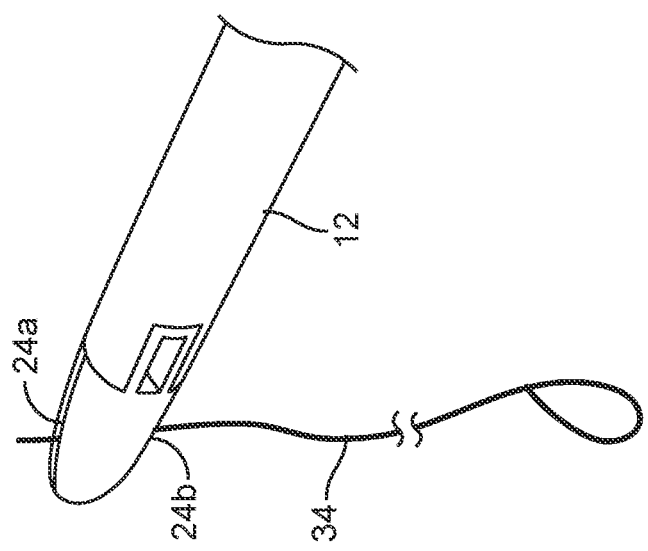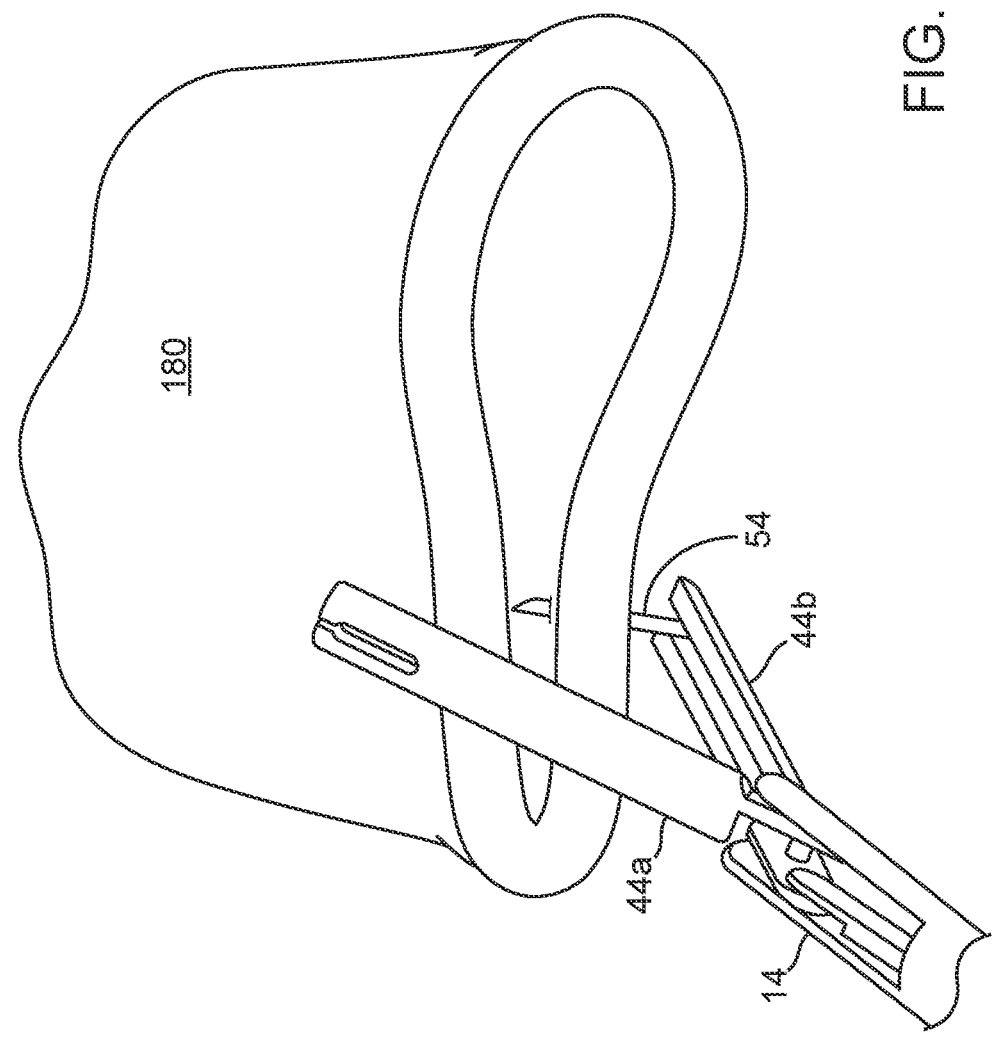
FIG. 29D

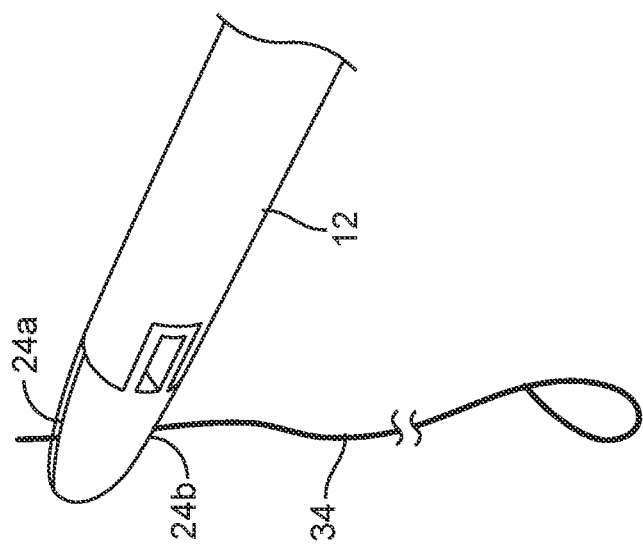
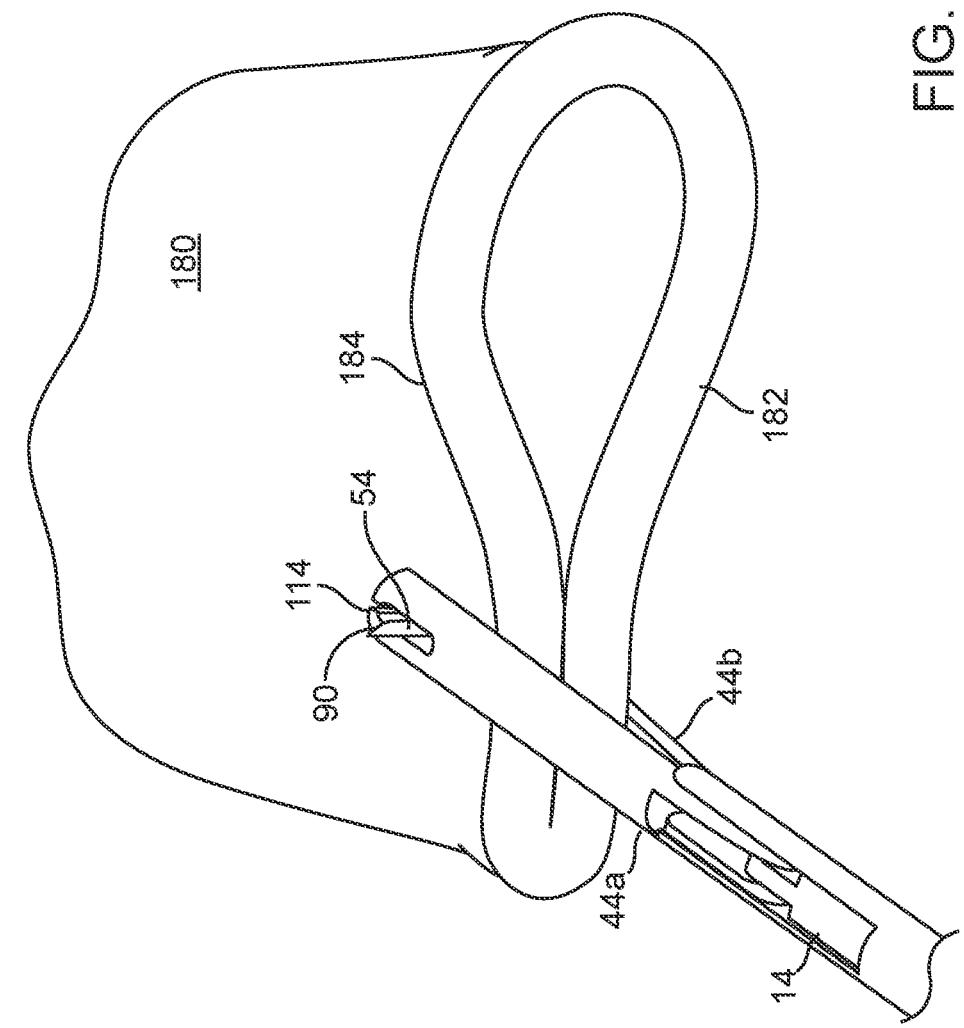
FIG. 29E

VAGINAL CUFF CLOSURE LAPAROSCOPIC SUTURE PASSER

RELATED APPLICATION DATA

The present application claims the benefit of priority to provisional application Ser. Nos. 62/986,257, filed on Mar. 6, 2020, and 62/992,017, filed Mar. 19, 2020, both of which are hereby incorporated herein by reference in their entirety.

FIELD

The present disclosure relates generally to surgical devices and surgical techniques, and more specifically, to laparoscopic tissue suturing devices and related methods.

BACKGROUND

Laparoscopic suturing is challenging and may take years for a surgeon to master. For example, suturing the vaginal cuff during a total laparoscopic hysterectomy (TLH) is one of the most challenging steps of TLH due to the dexterity and coordination required for suturing. In the United States alone, there are approximately 300,000 laparoscopic or robotic hysterectomies performed annually. In such procedures, the cervix is severed from the vagina and removed with the uterus, leaving behind the opening in the vaginal wall that must be closed. However, the geometry of this opening can make it difficult to suture effectively using laparoscopy tools. Consequently, vaginal cuff dehiscence, which is a potentially catastrophic event where the vaginal cuff opens such that the bowel may herniate through the vagina, may occur, thereby requiring immediate surgery. The incidence of vaginal cuff dehiscence after a TLH has been found to be approximately 0.5-4%. A modifiable risk factor for vaginal cuff dehiscence is surgical technique, which has significant inter-operator variability.

There, thus, remains a need to provide a more efficient and efficacious suturing instrument that minimizes inter-operator variability in laparoscopic suturing procedures, for example, post-TLH vaginal cuff suturing procedures.

SUMMARY

In accordance with one aspect of the present inventions, a laparoscopic suture passer comprises an elongated shaft (which may be rigid), a jaw assembly coupled to a distal end of the elongated shaft, and a hollow needle comprising a slotted bore extending along the entire length thereof. The jaw assembly comprises first and second jaw members hingedly associated with each other. The jaw members are configured for being alternately displaced relative to each other between an open position and a closed position. The jaw members may comprise opposing inner surfaces having teeth that intermesh together when the jaw members are displaced relative to each other from the open position to the closed position. The elongated shaft may be cylindrical, in which case, each of the jaw members may have a hemispherical cross-section, such that the jaw members, when in closed position, form a cylindrical member having a diameter that matches a diameter of the elongated shaft. The diameter of the elongated shaft may, e.g., be equal to or less than 5 mm. The hollow needle has a blunt end and a sharp end opposite the blunt end.

The blunt end of the hollow needle is hingedly coupled to the first jaw member for being alternately hinged between a retracted position, wherein the hollow needle is stowed in the first jaw member, and a deployed position, wherein the hollow needle extends away from the first jaw member. In one embodiment, a longitudinal axis of the hollow needle is parallel with a longitudinal axis of the first jaw member when the hollow needle is in the retracted position, and the longitudinal axis of the hollow needle is perpendicular to the longitudinal axis of the first jaw member when the hollow needle is in the deployed position. The slotted bore of the hollow needle may face distally when the hollow needle is in the deployed position.

In one embodiment, the sharp end of the deployed needle is configured for traversing the second jaw member as the jaw members are displaced relative to each other from the open position to the closed position. In this case, the jaw members may comprise cleaved distal tips respectively having open slots that form a contiguous slot in communication with the slot of the hollow needle when the jaw members are in the closed position, and the sharp end of the deployed needle may be configured for passing through the cleaved distal tip of the second jaw member. An optional embodiment of the laparoscopic suture passer further comprises a funnel having a base and a neck. The neck of the funnel is disposed at the blunt end of the needle, such that the funnel facilitates axial threading of a suture through the slotted bore of the needle when the suture is inserted into the base of the funnel.

In another embodiment, the laparoscopic suture passer further comprises a linkage assembly extending along the elongated shaft. The linkage assembly is affixed to the blunt end of the hollow needle, and the hollow needle is configured for being hinged from the retracted position to the deployed position in response to actuation of the linkage (e.g., by applying a tensile force to the linkage assembly). As one example, the linkage assembly may, e.g., comprise at least one wire. As another example, the linkage assembly may, e.g., comprise a sleeve slidably disposed relative to the elongated shaft, and the wire(s) may comprise at least two proximal wires coupled to a proximal end of the sleeve, and at a distal wire coupled between a distal end of the sleeve and the blunt end of the needle.

The laparoscopic suture passer may further comprise a handle and a slider mechanism operatively associated with the handle. The linkage assembly is operably coupled between the slider mechanism and the blunt end of the hollow needle, such that alternate displacement of the slider mechanism relative to the handle alternately hinges the hollow needle between the retracted position and the deployed position. The laparoscopic suture passer may further comprise a finger piece operably associated with the handle, and another linkage assembly operably coupled between the finger piece and at least one of the jaw members, such that alternately displacement of the finger piece relative to the handle alternately displaces the jaw members relative to each other between the open position and the closed position.

In accordance with a second aspect of the present inventions, a laparoscopic suturing system comprises the laparoscopic suture passer and a laparoscopic suture grasper.

In accordance with a third aspect of the present inventions, a method of suturing tissue (e.g., vaginal cuff) using the laparoscopic suture passer comprises introducing the laparoscopic suture passer through a laparoscopic port in a patient adjacent tissue to be sutured while the jaw members are in the closed position; displacing the first and jaw members relative to each other from the closed position to the open position; hinging the hollow needle from the retracted position to the deployed position; locating tissue to be sutured between the jaw members; displacing the jaw members relative to each other from the open position towards the closed position, such that the tissue is grasped between the jaw members while the hollow needle passes through the tissue (and optionally the cleaved tip of the second jaw member); axially threading a suture through the slotted bore of the hollow needle, such that the suture traverses the tissue; displacing the first and jaw members relative to each other towards the open position to release the tissue from the jaw members; and laterally removing the suture through the slotted bore of the hollow needle (and optionally through the open slots of the cleaved distal tips of the jaw members) while the suture traverses the tissue.

The method may optionally comprise introducing a laparoscopic suture grasper through another laparoscopic port in the patient, locating the laparoscopic suture grasper adjacent the tissue while the tissue is grasped between the jaw members, and using the laparoscopic suture grasper to axially thread the suture through the slotted bore of the hollow needle, and to laterally remove the suture from the slotted bore of the hollow needle (and optionally through the slots of the cleaved distal tips of the jaw members). Once suturing of the tissue is complete, the method may further comprise hinging the hollow needle from the deployed position to the retracted position, displacing the first and jaw members relative to each other from the open position to the closed position, and withdrawing the laparoscopic suture passer from the patient via the laparoscopic port while the jaw members are in the closed position.

In accordance with a fourth aspect of the present inventions, a method of suturing tissue using a laparoscopic tissue passer comprises positioning a first jaw member and a second jaw member of the laparoscopic tissue passer on opposite sides of the tissue (e.g., a vaginal cuff), displacing the first jaw member and the second jaw member towards each other, so that a hollow needle associated with one of the first jaw member and the second jaw member passes through the tissue, inserting a suture through an opening in the hollow needle while the hollow needle remains in the tissue, and removing the hollow needle from the tissue while the suture remains in the tissue. In one embodiment, the method further comprises introducing the laparoscopic tissue passer through a laparoscopic port. In another embodiment, the method further comprises, after the inserting step, passing an end of the suture through a loop at an opposite end of the suture.

Other and further aspects and features of embodiments of the disclosed inventions will become apparent from the ensuing detailed description in view of the accompanying figures.

BRIEF DESCRIPTION OF THE DRAWINGS

The drawings illustrate the design and utility of preferred embodiments of the present invention, in which similar elements are referred to by common reference numerals. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention, which is defined only by the appended claims and their equivalents. In addition, an illustrated embodiment of the disclosed inventions needs not have all the aspects or advantages shown. An aspect or an advantage described in conjunction with a particular embodiment of the disclosed inventions is not necessarily limited to that embodiment and can be practiced in any other embodiments even if not so illustrated. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 8 is a bottom view of the distal end of the laparoscopic suture passer of FIG. 2;

FIG. 9 is a top view of the distal end of the laparoscopic suture passer of FIG. 2;

FIG. 10 is a profile of the distal end of the laparoscopic suture passer of FIG. 2, particularly showing the jaw members in the closed position, wherein the shaft of the laparoscopic suture passer is shown in phantom;

FIG. 11 is a profile of the distal end of the laparoscopic suture passer of FIG. 2, particularly showing the jaw members in the open position, wherein the shaft of the laparoscopic suture passer is shown in phantom;

FIG. 13 is a profile of the distal end of the laparoscopic suture passer of FIG. 2, particularly showing the jaw members in the closed position and the needle in the retracted position, wherein the lower jaw member of the laparoscopic suture passer is shown in phantom;

FIG. 14 is a profile of the distal end of the laparoscopic suture passer of FIG. 2, particularly showing the jaw members in the open position and the needle in the deployed position, wherein the lower jaw member of the laparoscopic suture passer is shown in phantom;

FIG. 19 is a profile view of the distal end of another exemplary laparoscopic suture passer used in the laparoscopic suturing system of FIG. 1, particularly showing the jaw members of the laparoscopic suture passer in an open position, while a needle of the laparoscopic suture passer is in a deployed position;

FIG. 20 is a bottom view of the distal end of the laparoscopic suture passer of FIG. 19;

FIG. 21 is a perspective view of the laparoscopic suture passer of FIG. 19,

FIG. 22 is a perspective view of a linkage mechanism used to displace the upper jaw member relative to the lower jaw member of the laparoscopic suture passer of FIG. 19;

DETAILED DESCRIPTION OF THE ILLUSTRATED EMBODIMENTS

Figure 1:
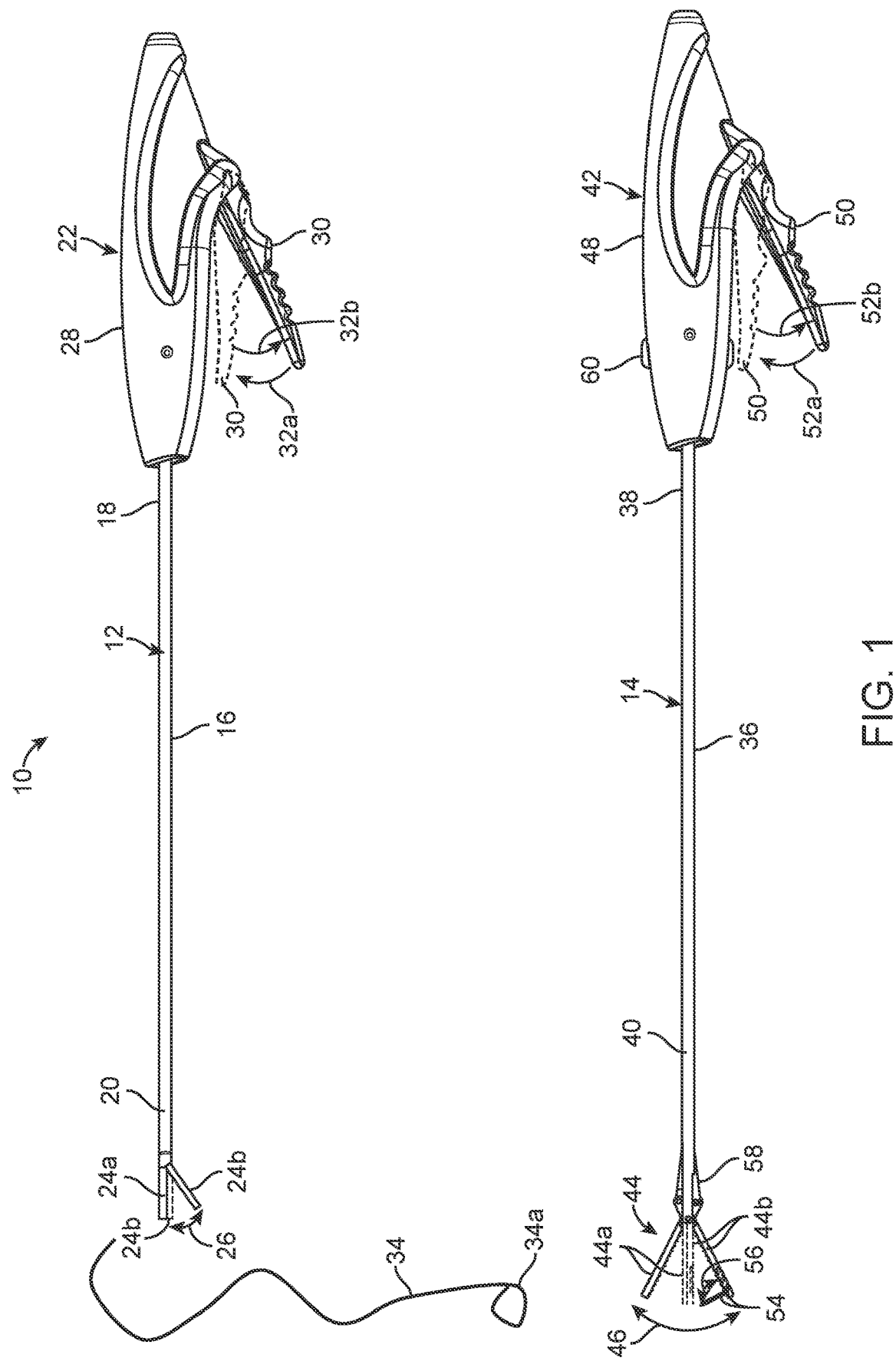
FIG. 1 is a schematic diagram of an exemplary laparoscopic suturing system constructed in accordance with one embodiment of the present inventions.

Referring to FIG. 1, one embodiment of a laparoscopic suturing system 10 generally comprises a laparoscopic suture grasper 12 and a laparoscopic suture passer 14 that are operated in coordination to suture tissue (such as, e.g., a vaginal cuff) during a laparoscopic suturing procedure.

The laparoscopic suture grasper 12 comprises an elongated, hollow, rigid shaft 16 having a proximal end 18 and a distal end 20, a handle assembly 22 coupled to the proximal end 18 of the shaft 16, and a pair of opposable upper and lower jaw members 24a, 24b coupled to the distal end 20 of the shaft 16.

The shaft 16 preferably is cylindrical (i.e., has a circular cross-section), although in alternative embodiments, the shaft 16 may have any suitable cross-sectional geometry. The shaft 16 is preferably narrow enough (e.g., less than 10 mm in diameter, and preferably 5 mm or less in diameter), such that the laparoscopic suture grasper 12 may be introduced through a conventional laparoscopic port (not shown) into a patient. The shaft 16 may have a suitable length, e.g., in the range of 18 cm-45 cm.

In the illustrated embodiment, the upper jaw member 24a is immovably affixed to the distal end 20 of the shaft 16, whereas the lower jaw member 24b is pivotably affixed to the distal end 20 of the shaft 16 (e.g., via a pivot pin (not shown)), such that the jaw members 24a, 24b may be alternately displaced relative to each other (shown by the arrow 26) between a closed position (shown in phantom) and an open position. In alternative embodiments, the lower jaw member 24b may be immovably affixed to the distal end 20 of the shaft 16, whereas the upper jaw member 24a may pivotably affixed to the distal end 20 of the shaft 16, or both jaw members 24a, 24b may be pivotably affixed to the distal end 20 of the shaft 16.

While in the closed position, the jaw members 24a, 24b preferably have a profile that is equal to or less than the diameter of the shaft 16, such that the jaw members 24a, 24b, along with the shaft 26, may be introduced through the laparoscopic port. After introduction through the laparoscopic port, the jaw members 24a, 24b may then be placed into the higher profile open position. Thus, while the jaw members 24a, 24b are in the closed position, the laparoscopic suture grasper 12 may be introduced through a laparoscopic port (not shown) into the patient, then displaced away from each other into the open position prior to grasping a suture 34, displaced toward each other into the closed position to grasp the suture 34, and the displaced away from each other into the open position again to release the suture 34. In the illustrated embodiment, the suture 34 has a looped end 34a through which the opposite end of the suture 34a may be passed to create the first stitch, as will be described in further detail below.

The handle assembly 22 comprises a handle 28 configured for being ergonomically grasped by the palm of a single hand, and a pivotable finger piece 30 configured for being ergonomically grasped by the fingers of the hand. The finger piece 30 is pivotably affixed to the handle 28 and is operably associated with the opposable jaw members 24a, 24b via a linkage (e.g., a reciprocating rod (not shown)) extending through the shaft 16. Manual displacement of the pivotable finger piece 30 towards the handle 28 (shown by the arrow 32a) pivots the lower jaw member 24b towards the upper jaw member 24a to the closed position, such that the suture 34 may be grasped between the jaw members 24a, 24b, while manual displacement of the pivotable finger piece 30 away from the handle 28 (shown by the arrow 32b), e.g., by firmly grasping the handle 28 and releasing the finger piece 30 with the fingers, pivots the lower jaw member 24b away from the upper jaw member 24a to the open position, such that the suture 34 may be released by the jaw members 24a, 24b.

The pivotable finger piece 30 may be biased away from the handle 28, e.g., via a spring mechanism (not shown), such that the jaw members 24a, 24b are biased to the open position. In this case, the pivotable finger piece 30 may be manually pivoted towards the handle 28 (e.g., by firmly grasping the handle 28 and squeezing the finger piece 30 with the fingers) in opposition to the biasing force applied by the spring mechanism to place the jaw members 24a, 24b in the closed position. An optional locking mechanism (e.g., a ratchet (not shown)) may be employed to lock the jaw members 24a, 24b in any position between the open position and the closed position, and then operated to unlock the jaw members 24a, 24b to allow the biasing force applied to the pivotable finger piece 30 (e.g., by grasping the handle 28 and releasing the finger piece 30 with the fingers) to place the jaw members 24a, 24b in the open position.

It should be appreciated that, although a handle 28, pivotable finger piece 30, and associated push rod are described as actuating the jaw members 24a, 24b between the open position and the closed position, any suitable proximal actuator and associated linkage may be used to alternately close and open the jaw members 24a, 24b in a manner such that the suture 34 may be alternately grasped and released. For example, the handle assembly 22 may alternatively comprise a first finger ring (not shown) immovably affixed to the proximal end 18 of the shaft 16, and a second finger ring (not shown) pivotably affixed to the proximal end 18 of the shaft 16, such that alternate manual displacement of the finger rings towards and away from each other alternately closes and opens the jaw members 24a, 24b.

The laparoscopic suture passer 14 comprises an elongated, hollow, rigid shaft 36 having a proximal end 38 and a distal end 40, a handle assembly 42 affixed to the proximal end 38 of the shaft 36, a jaw assembly 44 including a pair of opposable upper and lower jaw members 44a, 44b hingedly associated with each other, such that the jaw members 44a, 44b may be displaced between a closed position (shown in phantom in FIG. 1), and an open position, and a needle 54 operatively associated with the jaw members 44a, 44b, such that the needle 54 may be displaced between a retracted position (shown in phantom in FIG. 1) and a deployed position (shown by the arrow 56).

Like the shaft 16 of the laparoscopic suture grasper 12, the shaft 36 of the laparoscopic suture passer 14 is preferably cylindrical (i.e., has a circular cross-section), although in alternative embodiments, may have any suitable cross-sectional geometry; is preferably narrow enough (e.g., less than 10 mm in diameter, and preferably 5 mm or less in diameter), such that the laparoscopic suture passer 14 may be introduced through a separate conventional laparoscopic port (not shown) into the patient; and may have a suitable length, e.g., in the range of 18 cm-45 cm.

Figure 2:
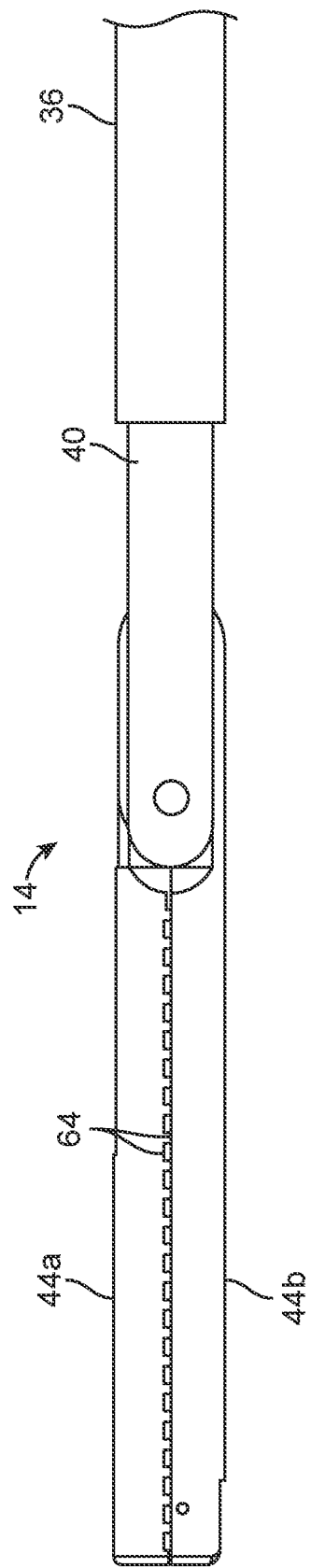
FIG. 2 is a profile view of the distal end of an exemplary laparoscopic suture passer used in the laparoscopic suturing system of FIG. 1, particularly showing the jaw members of the laparoscopic suture passer in a closed position, while a needle of the laparoscopic suture passer is in a retracted position.
Figure 3:
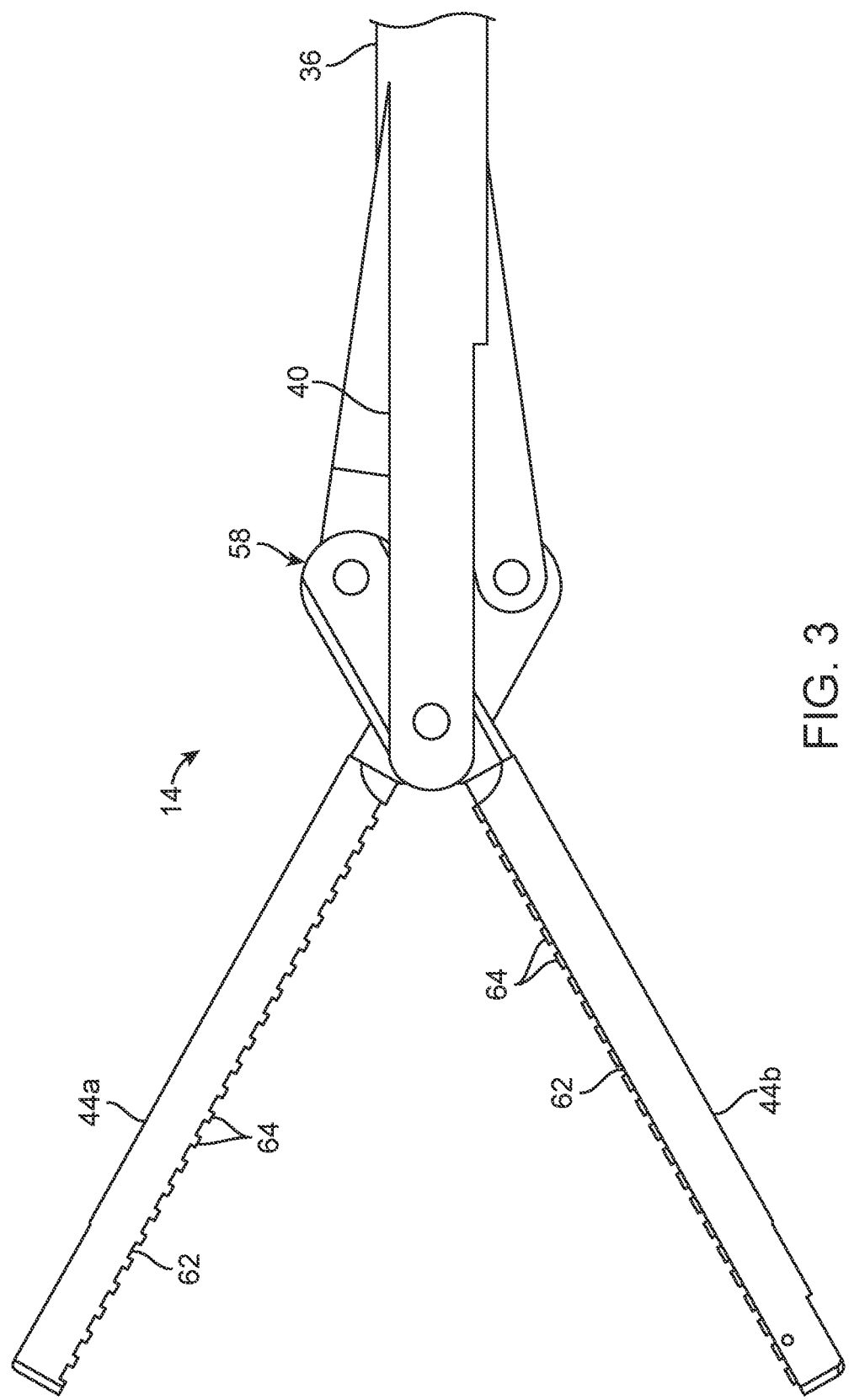
FIG. 3 is a profile view of the distal end of the laparoscopic suture passer of FIG. 2, particularly showing the jaw members in an open position, while the needle is in a retracted position.
Figure 4:
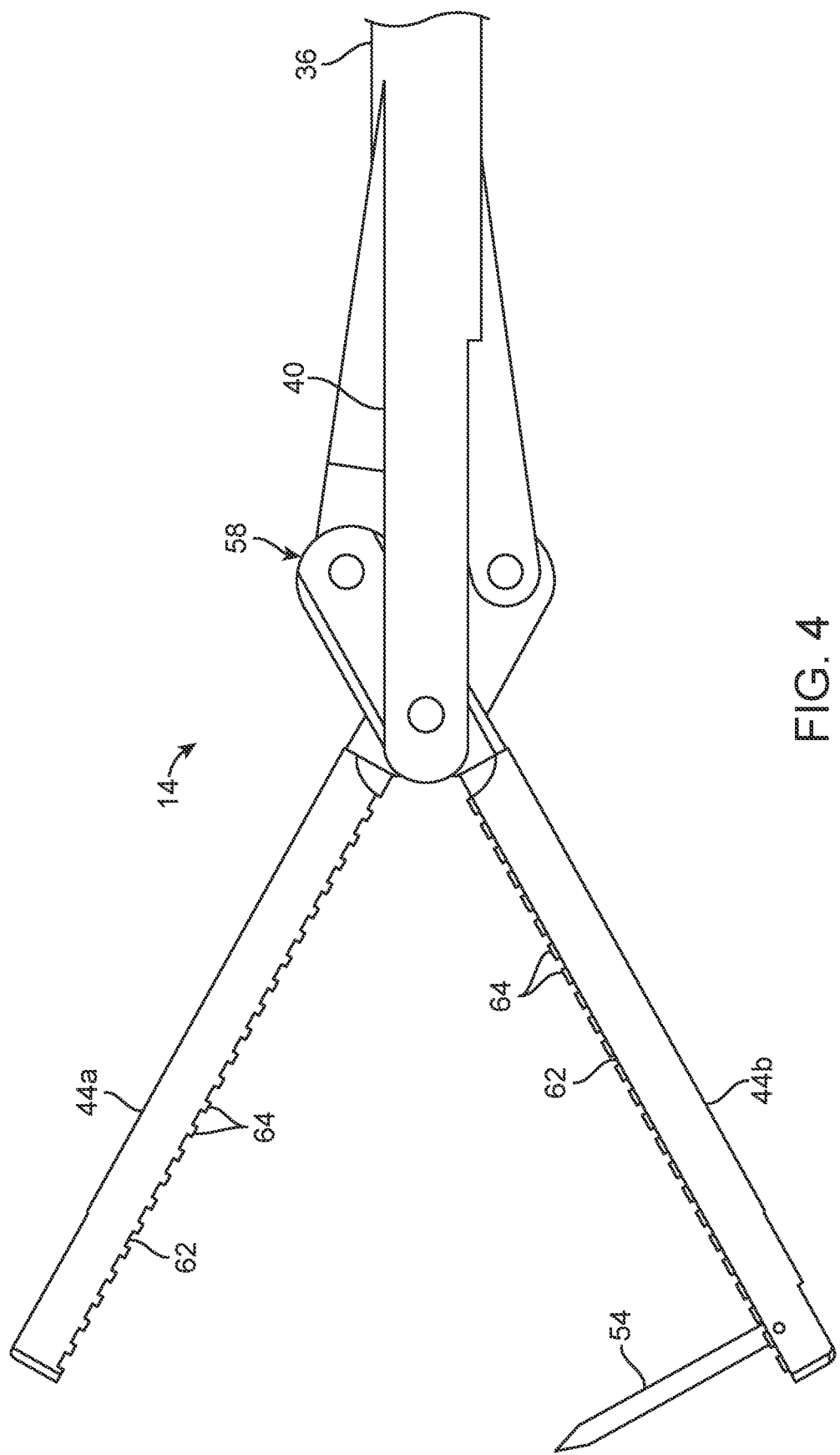
FIG. 4 is a profile view of the distal end of the laparoscopic suture passer of FIG. 2, particularly showing the jaw members in the open position, while the needle is in a deployed position.

In the illustrated embodiment, both jaw members 44a, 44b are pivotably affixed to the distal end 40 of the shaft 36, such that the jaw members 44a, 44b may be alternately displaced relative to each other (shown by the arrow 46) between the closed position (see FIGS. 2 and 5), and the open position (see FIGS. 3 and 4). Pivoting both jaw members 44a, 44b about the distal end 40 of the shaft 36 maximizes displacement of the jaw members 44a, 44b relative to each other to provide clearance for displacing the needle 54 between the retracted position and the deployed position, as will be described in further detail below. However, in an alternative embodiment described in further detail below, one of the jaw members 44a, 44b may be immovably affixed to the distal end 40 of the shaft 36, whereas the other one of the jaw members 44a, 44b may be pivotably affixed to the distal end 40 of the shaft 36. Ultimately, the jaw members 44a, 44b may be arranged in any suitable manner with the distal end 40 of the shaft 36 as long as the needle 54 may be displaced between the retracted position and the deployed position.

The handle assembly 42 comprises a handle 48 configured for being ergonomically grasped by the palm of a hand, and a finger piece 50 configured for being ergonomically grasped by the fingers of the hand. The finger piece 50 is pivotably affixed to the handle 48 and is operably associated with the opposable jaw members 44a, 44b via a linkage 58 extending through the shaft 36. Further details on the linkage 58 will be described in further detail below. Manual displacement of the pivotable finger piece 50 towards the handle 48 (shown by the arrow 52a) pivots the jaw members 44a, 44b toward each other to the closed position, while manual displacement of the pivotable finger piece 50 away from the handle 48 (shown by arrow 52b) pivots the jaw members 44a, 44b away from each other to the open position.

The pivotable finger piece 50 may be biased away from the handle 48, e.g., via a spring mechanism (not shown), such that the jaw members 44a, 44b are biased to the open position. In this case, the pivotable finger piece 50 may be manually pivoted towards the handle 48 (e.g., by firmly grasping the handle 48 and squeezing the finger piece 50 with the fingers) in opposition to the biasing force applied by the spring mechanism to place the jaw members 44a, 44b in the closed position. The jaw members 44a, 44b can also be operated in different positions between the open position and the closed position to grasp and release tissue of varying thickness via incremental manual displacement of the pivotable finger piece 50 towards or away from the handle 48. An optional locking mechanism (e.g., a ratchet (not shown)) may be employed to lock the jaw members 44a, 44b in any position between the open position and the closed position, and then operated to unlock the jaw members 44a, 44b to allow the biasing force applied to the pivotable finger piece 50 (e.g., by grasping the handle 48 and releasing the finger piece 50 with the fingers) to place the jaw members 44a, 44b in the open position.

Figure 6:
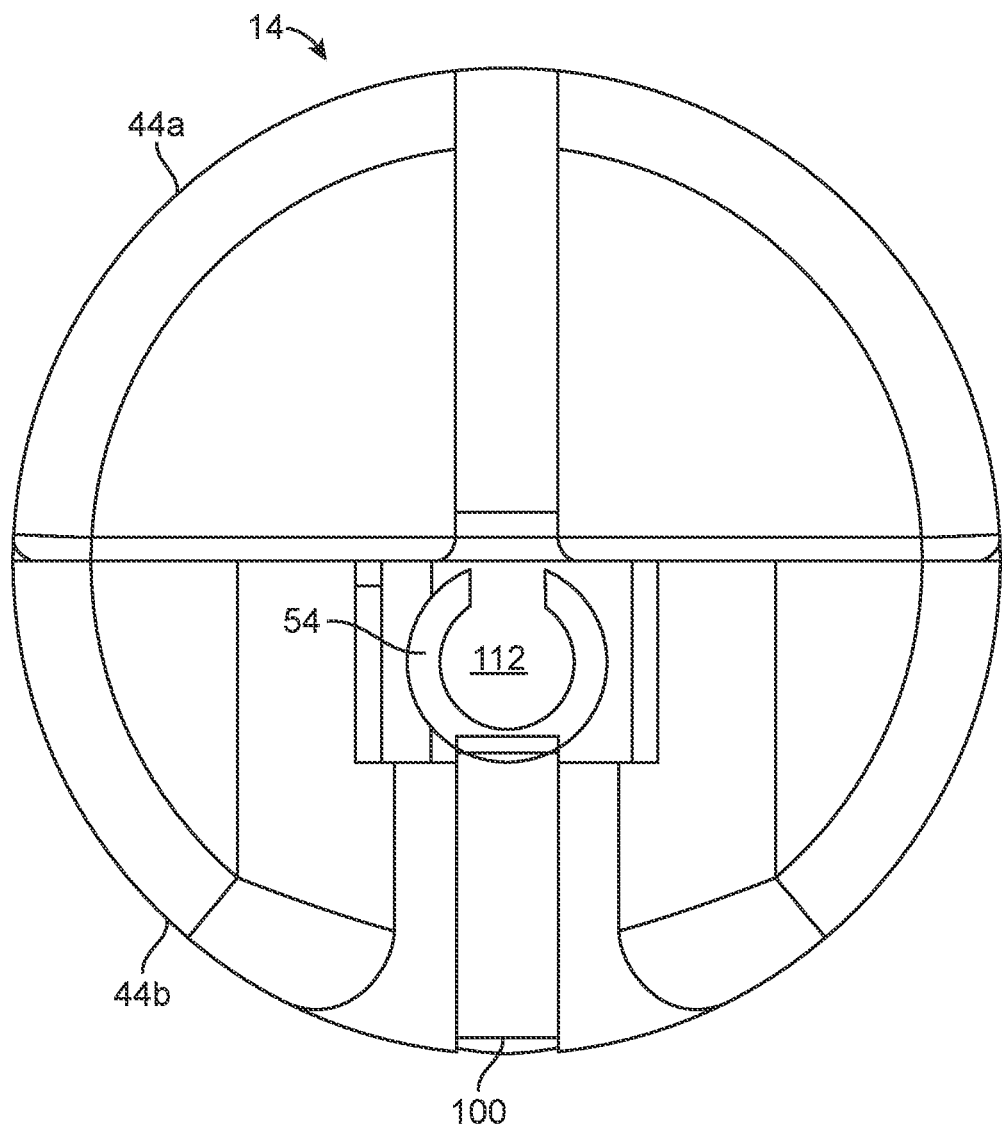
FIG. 6 is an axial view of the jaw members of the laparoscopic suture passer of FIG. 2, while the jaw members are in the closed position.

While in the closed position, the jaw members 44a, 44b preferably have a profile that is equal to or less than the diameter of the shaft 36, such that the jaw members 44a, 44b, along with the shaft 36, may be introduced through the laparoscopic port. As best shown in FIG. 6, each of the jaw members 44a, 44b preferably has a hemi-spherical cross-section, with the diameters of the hemi-spherical cross-sections facing inward toward each other, such that the jaw members 44a, 44b, when in the closed position, form a cylindrical member having a diameter that matches the diameter of the shaft 36 (i.e., the outer envelopes of the shaft 36 and closed jaw members 44a, 44b are contiguous).

Figure 5:
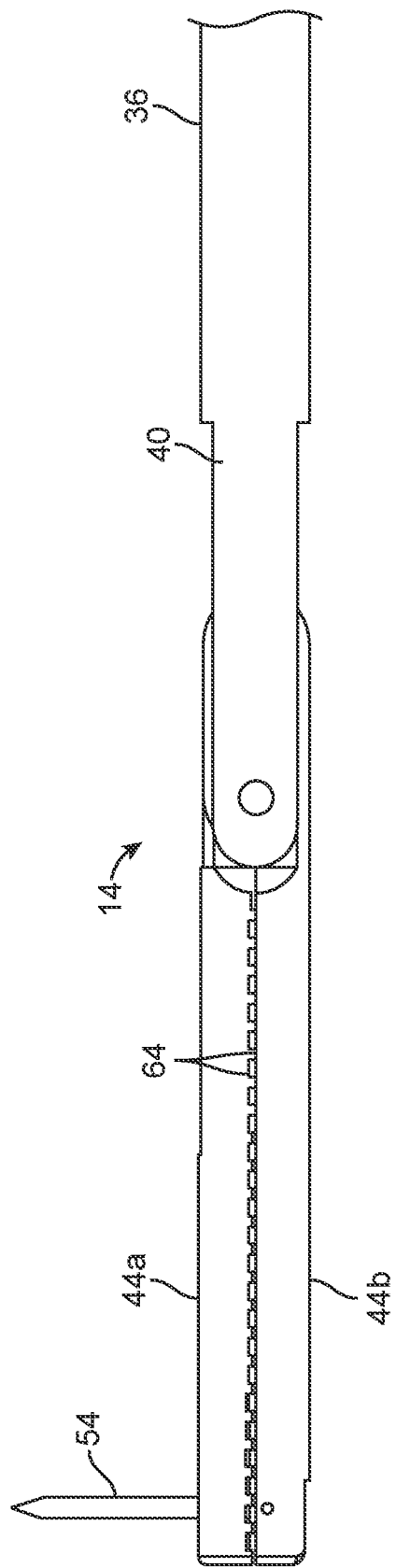
FIG. 5 is a profile view of the distal end of the laparoscopic suture passer of FIG. 2, particularly showing the jaw members in the closed position, while the needle is in the deployed position.
Figure 7:
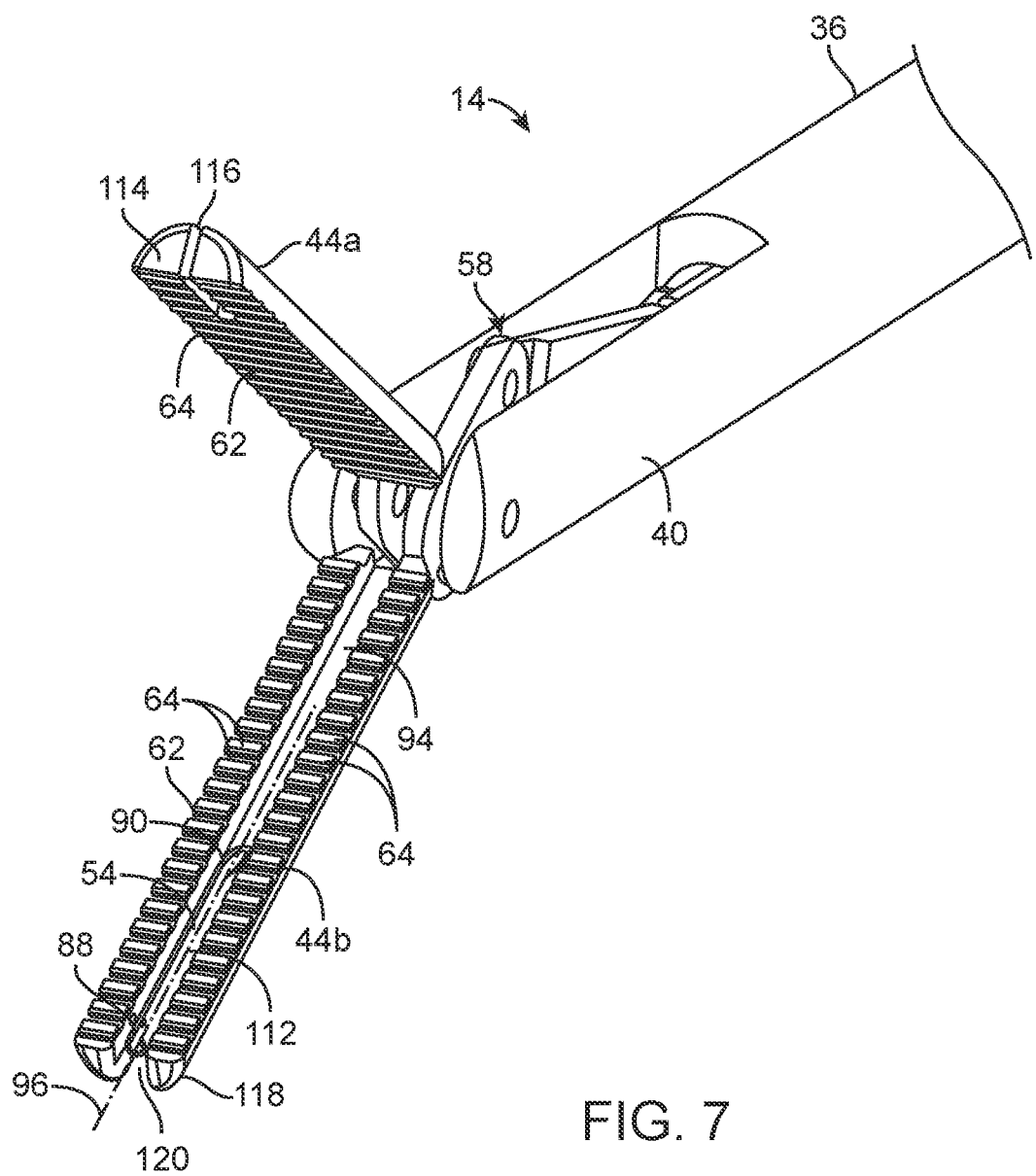
FIG. 7 is a perspective view of the jaw members of the laparoscopic suture passer of FIG. 2, while the jaw members are in the open position.

The jaw members 44a, 44b respectively comprise opposing inner surfaces 62 that are textured, and in particular, have teeth $64_{[M1]}$, to facilitate grasping of tissue between the jaw members 44a, 44b, as best shown in FIG. 7. In the illustrated embodiment, teeth 64 of the upper jaw member 44a intermesh together with the teeth 64 of the lower jaw member 44b when the jaw members 44a, 44b are in the closed position, as best shown in FIGS. 2 and 5. In this manner, the jaw members 44a, 44b have an integrated outer cylindrical surface that matches the outer cylindrical surface of the shaft 36.

Referring to FIGS. 8-12, the linkage 58 between the pivotable finger piece 50 (shown in FIG. 12) and the jaw members 44a, 44b comprises a generally cylindrical reciprocating rod 66 that resides within a main central lumen 76 extending through the shaft 36 (shown in FIGS. 10 and 11), a pair of flattened rigid links 72a, 72b operatively associated with the reciprocating rod 66, and a pair of flattened rigid links 74a, 74b respectively integrated with the jaw members 44a, 44b. In the illustrated embodiment, the reciprocating rod 66 has a flattened distal end 70 to which the pair of rigid links 72a, 72b are pivotably coupled, as shown in FIGS. 10 and 11). As best shown in FIGS. 8 and 9, the distal end 40 of the shaft 36 is cleaved to form two parallel arms 76 for supporting the pair of rigid links 72a, 72b and pair of rigid links 74a, 74b therebetween. In particular, the rigid links 74a, 74b are pivotably coupled between the distal parallel arms 76 of the shaft 36 via a single pivot pin 78. The pair of rigid links 72a, 72b are pivotably coupled between the distal end 70 of the reciprocating rod 66 and the rigid links 74a, 74b respectively via a single pivot pin 80 and two pivot pins 82a, 82b.

Figure 12:
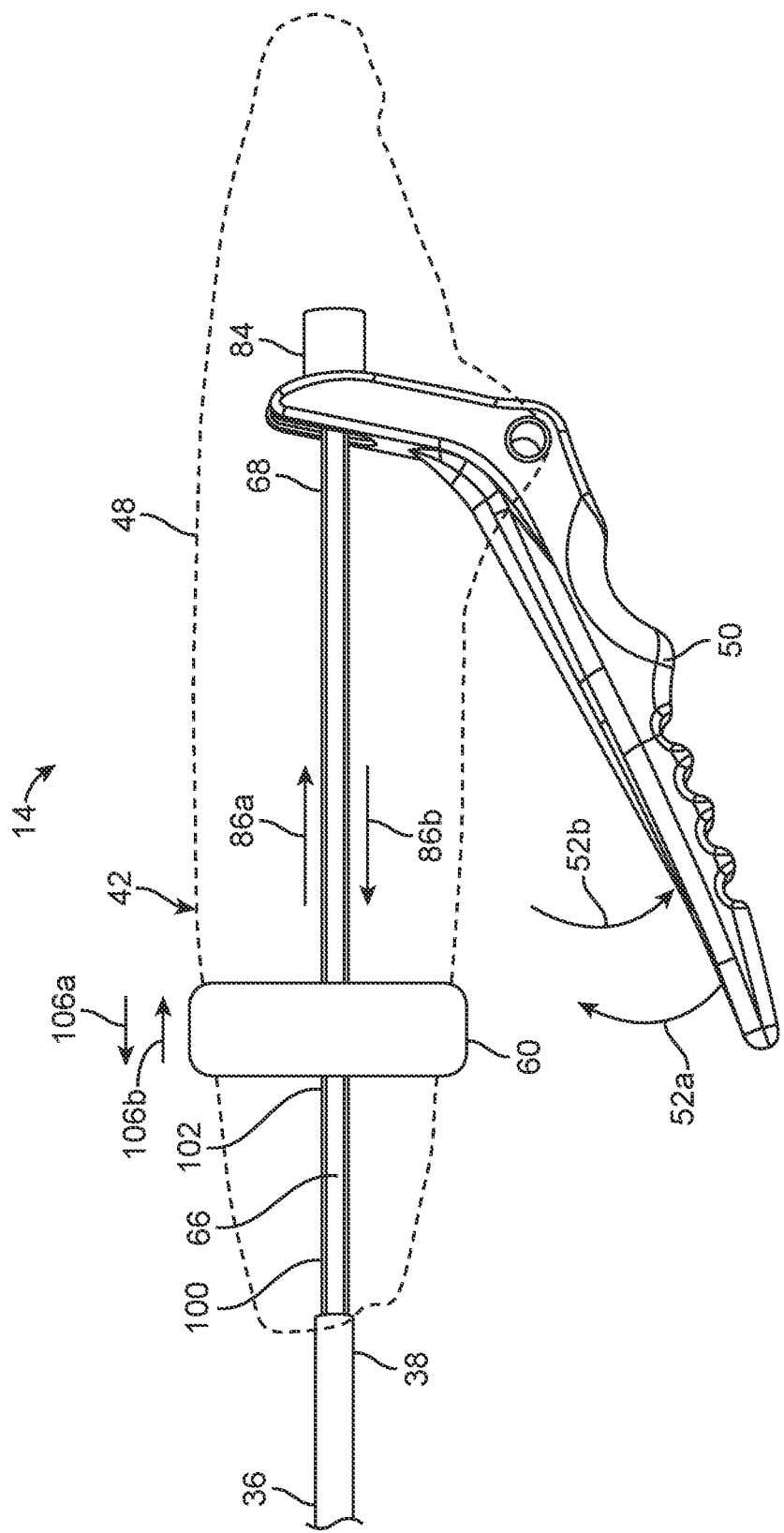
FIG. 12 is a profile view of handle assembly of the laparoscopic suture passer of FIG. 2, wherein the handle of the handle assembly is shown in phantom.

In the embodiment illustrated in FIG. 12, the linkage 58 comprises a boss 84 affixed to the proximal end 68 of the reciprocating rod 66. The proximal end 68 of the reciprocating rod 66 extends through the pivotable finger piece 50, with the boss 84 located proximal to the pivotable finger piece 50 and in an interference relationship with the pivotable finger piece 50. When the pivotable finger piece 50 is pivoted toward the handle 48 (shown by the arrow 52a), the reciprocating rod 66 is proximally displaced (shown by the arrow 86a) within the central lumen 52 of the shaft 36. Conversely, when the pivotable finger piece 50 is pivoted away from the handle 48 (shown by the arrow 52b), the reciprocating rod 66 is distally displaced (shown by the arrow 86b) within the central lumen 52 of the shaft 36.

Thus, displacement of the reciprocating rod 66 in the distal direction 86b in response to displacing the pivotable finger piece 50 towards the handle 48 (shown by the arrow 52a in FIG. 12), causes the rigid links 72a, 72b and rigid links 74a, 74b to pivot outwards away from the distal end 40 of the shaft 36 (i.e., the rigid link 72a and rigid link 74a outwardly pivot relative to each other, and the rigid link 72b and rigid link 74b outwardly pivot relative to each other), thereby displacing the jaw members 44a, 44b away from each other towards the open position, as best shown in FIG. 11. Conversely, displacement of the reciprocating rod 66 in the proximal direction 86a in response to displacing the pivotable finger piece 50 away from handle 48 (shown by the arrow 52b in FIG. 12), causes the rigid links 72a, 72b and rigid links 74a, 74b to pivot inwards toward the distal end 40 of the shaft 36 (i.e., the rigid link 72a and rigid link 74a inwardly pivot relative to each other, and the rigid link 72b and rigid link 74b inwardly pivot relative to each other), thereby displacing the jaw members 44a, 44b toward each other to the closed position, as best shown in FIG. 10.

Notably, as shown in FIG. 10, the rigid links 72a, 72b and rigid links 74a, 74b reside completely between the distal parallel arms 76 of the shaft 36 (i.e., the links 72a, 72b and rigid links 74a, 74b do not protrude outwardly from the circular cross-sectional envelope of the shaft 36) when the jaw members 44a, 44b are in the closed position, thereby maintaining the low profile of the laparoscopic suture passer 14. It should be appreciated that, although the finger piece 50 and associated linkage (including the reciprocating rod 66, rigid links 72a, 72b, and rigid links 74a, 74b) are described as actuating the jaw members 44a, 44b between the open position and the closed position, any suitable proximal actuator and associated linkage may be used to alternately displace the jaw members 44a, 44b between the open position and closed position. For example, the handle assembly 42 may alternatively comprise a first finger ring (not shown) immovably affixed to the proximal end 38 of the shaft 36, and a second finger ring (not shown) pivotably affixed to the proximal end 38 of the shaft 36, such that alternate manual displacement of the finger rings towards and away from each other alternately closes and opens the jaw members 44a, 44b.

As shown in FIGS. 7, 13, and 14, the needle 54 comprises a blunt end 88 and a sharp tissue penetrating end 90 opposite of the blunt end 88. The blunt end 88 of the needle 54 is hingedly coupled to the lower jaw member 44b via a pivot pin 92, such that the needle 54 may be alternately hinged (shown by the arrows 52a, 52b in FIG. 1) between the retracted position (see FIG. 13) and a deployed position (see FIG. 14). When in the retracted position, the needle 54 is stowed within the lower jaw member 44b, and when in the deployed position, the needle 54 extends away from lower jaw member 44b toward the upper jaw member 44a.

To facilitate placement of the jaw members 44a, 44b into the closed position when the needle 54 is in the retracted position, the lower jaw member 44b comprises storage channel 94 in which the retracted needle 54 may be seated, as illustrated in FIG. 7. In the illustrated embodiment, the storage channel 94 is disposed in the inner surface 62 along the longitudinal axis 96 of the lower jaw member 44b and between the two rows of teeth 64. In alternative embodiments, the blunt end 88 of the needle 54 may be hingedly coupled to the upper jaw member 44a via a pivot pin, such that, when in the retracted position, the needle 54 extends along the upper jaw member 44a when the jaw members 44a, 44b are in the closed position, and, when in the deployed position, the needle 54 extends from the upper jaw member 44a toward the lower jaw member 44b.

In the illustrated embodiment, when in the retracted position, the longitudinal axis 98 of the needle 54 is generally parallel to the longitudinal axis 96 of the lower jaw member 44b, with the sharp end 90 of the needle 54 pointing proximally along the longitudinal axis 96 of the lower jaw member 44b. In one alternative embodiment, the longitudinal axis 98 of the needle 54 may be arranged at a non-parallel angle (i.e., more than 0 degrees) relative to the longitudinal axis 96 of the lower jaw member 44b when in the retracted position. In another alternative embodiment, the sharp end 90 of the needle 54 may point distally along the longitudinal axis 96 of the lower jaw member 44b when in the retracted position.

In the embodiment illustrated in FIG. 14, when in the deployed position, the longitudinal axis 98 of the needle 54 extends perpendicularly to the longitudinal axis 96 of the lower jaw member 44b, with the sharp end 90 of the needle 54 pointing generally towards the upper jaw member 44a. In alternative embodiments, the longitudinal axis 98 of the needle 54 may be arranged obliquely relative to the longitudinal axis 96 of the lower jaw member 44b, as long as the sharp end 90 of the needle 54 is capable of penetrating tissue disposed between the jaw members 44a, 44b when the jaw members 44a, 44b are displaced from the open position towards the closed position.

The handle assembly 42 further comprises a slider mechanism 60 (shown in FIG. 1) associated with the handle 48 for displacing the needle 54 between the retracted position and the deployed position, as will be described in further detail below. The needle 54 is actuated to hinge between the retracted position (FIG. 13) and the deployed position (FIG. 14) via a suitable linkage assembly operably associated with the slider mechanism 60, which in the illustrated embodiment, comprises an elongated member in the form of a push-pull wire 100. The push-pull wire 100 has a distal end 104 that is affixed to the blunt end 88 of the needle 54, such that the pivot pin 92 is disposed between the location of the blunt end 88 where the distal end 98 of the push-pull wire 100 is affixed and the sharp end 90 of the needle 54. Preferably, the distal end 104 of the push-pull wire 100 is affixed to the extremity of the blunt end 88 in order to maximize leverage when hinging the needle 54 between the retracted position and the deployed position.

As illustrated in FIG. 12, the push-pull wire 100 has a proximal end 102 that is affixed to the slider mechanism 60 disposed on the proximal end 38 of the shaft 36 (or alternatively on the handle 48). Manual displacement of the slider mechanism 60 relative to the handle 48 from a distal position to a proximal position (along the arrow 106a) axially displaces the push-pull wire 100 in the proximal direction, thereby hinging the needle 54 from the retracted position into the deployed position, while manual displacement of the slider mechanism 60 relative to the handle 48 from a proximal position to a distal position (along the arrow 106b) axially displaces the push-pull wire 100 in the distal direction, thereby hinging the needle 54 from the deployed position back into retracted position. In an optional embodiment, a locking mechanism or spring mechanism (not shown) may be employed in the handle 48 for locking the slider mechanism 60 in the proximal position, and thus, locking the needle 54 in the deployed position.

Figure 15:
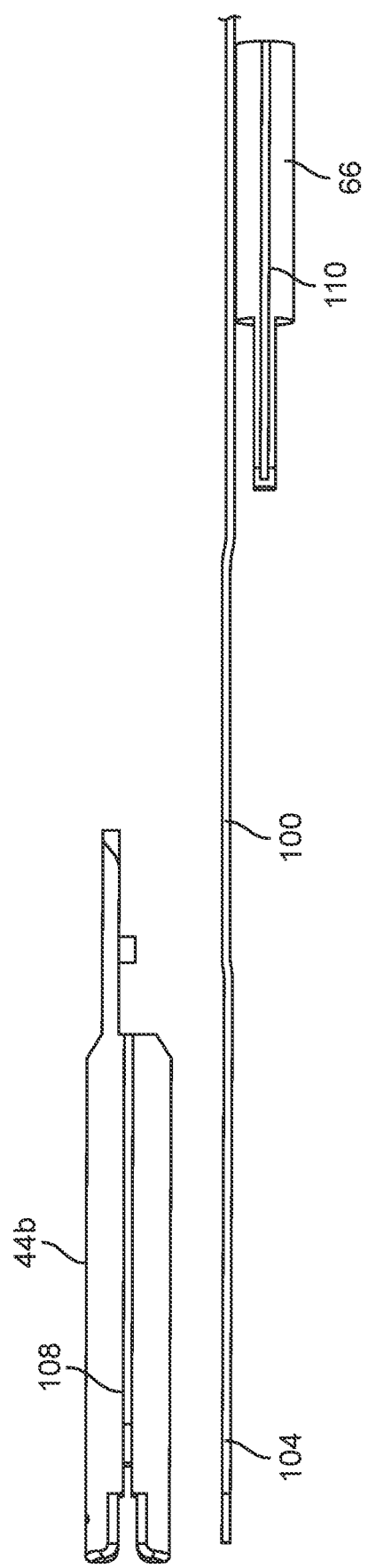
FIG. 15 is an exploded view of the lower jaw member, push-pull wire, and reciprocating shaft of the laparoscopic suture passer of FIG. 2.

In the illustrated embodiment, the push-pull wire 100 has the necessary columnar strength to resist buckling when displaced in the distal direction in response to manual displacement of the slider mechanism 60 relative to the handle 48 from the proximal position to the distal position. As illustrated in FIGS. 8 and 15, push-pull wire 100 extends from the blunt end 88 of the needle 54 in the proximal direction along an open pull wire channel 108 that longitudinally runs along the bottom surface of the lower jaw member 44b, and along an open pull wire channel 110 that longitudinally runs along the bottom surface of the rod 66 (or alternatively along the top surface of the upper jaw member 44a and the top surface of the rod 66 if the needle 40 is coupled to the upper jaw member 44a). Alternatively, instead of running along the open wire channel 110 on the bottom surface of the rod 66, the push-pull wire 100 may be slidably disposed through a wire lumen (not shown) that longitudinally extend through the shaft 36 separately from the central lumen 76 of the shaft 36. In the illustrated embodiment, the push-pull wire 100 is flattened, and the wire channels 108, 110 are rectangular, such that the push-pull wire 100 conforms to and is guided within the wire channels 108, 110. Thus, it can be appreciated that the wire channels 108, 110 (or alternatively the pull wire lumen) provide support to the push-pull wire 100, thereby further ensuring that the push-pull wire 100 does not axially buckle when displaced in the distal direction. In an alternative embodiment, if the push-pull wire 100 does not have sufficient columnar strength to prevent buckling when displaced in the distal direction, a spring mechanism (not shown) may be disposed in the lower jaw member 44b for biasing the needle 54 into the retracted position, and an additional spring mechanism (not shown) associated with the slider mechanism 60 may be disposed in the handle 48 to maintain slight tensioning of the push-pull wire 100.

Significantly, the jaw members 44a, 44b and needle 54 are designed in a manner, such that the sharp end 90 of the needle 54, when in the deployed position, traverses the lower jaw member 44b when the jaw members 44a, 44b are displaced from the open position towards the closed position, such that the sharp end 90 of the needle 54 passes through tissue as the tissue is grasped between the jaw members 44a, 44b. Furthermore, the jaw members 44a, 44b and needle 54 are designed in a manner, such that the suture 34 may be axially threaded through the longitudinal axis 94 of the needle 54, and thus through the tissue between the jaw members 44a, 44b to create a stitch, and then decoupled from the laparoscopic suture passer 14 while the suture 34 remains in place the tissue to preserve the stitch.

Figure 16:
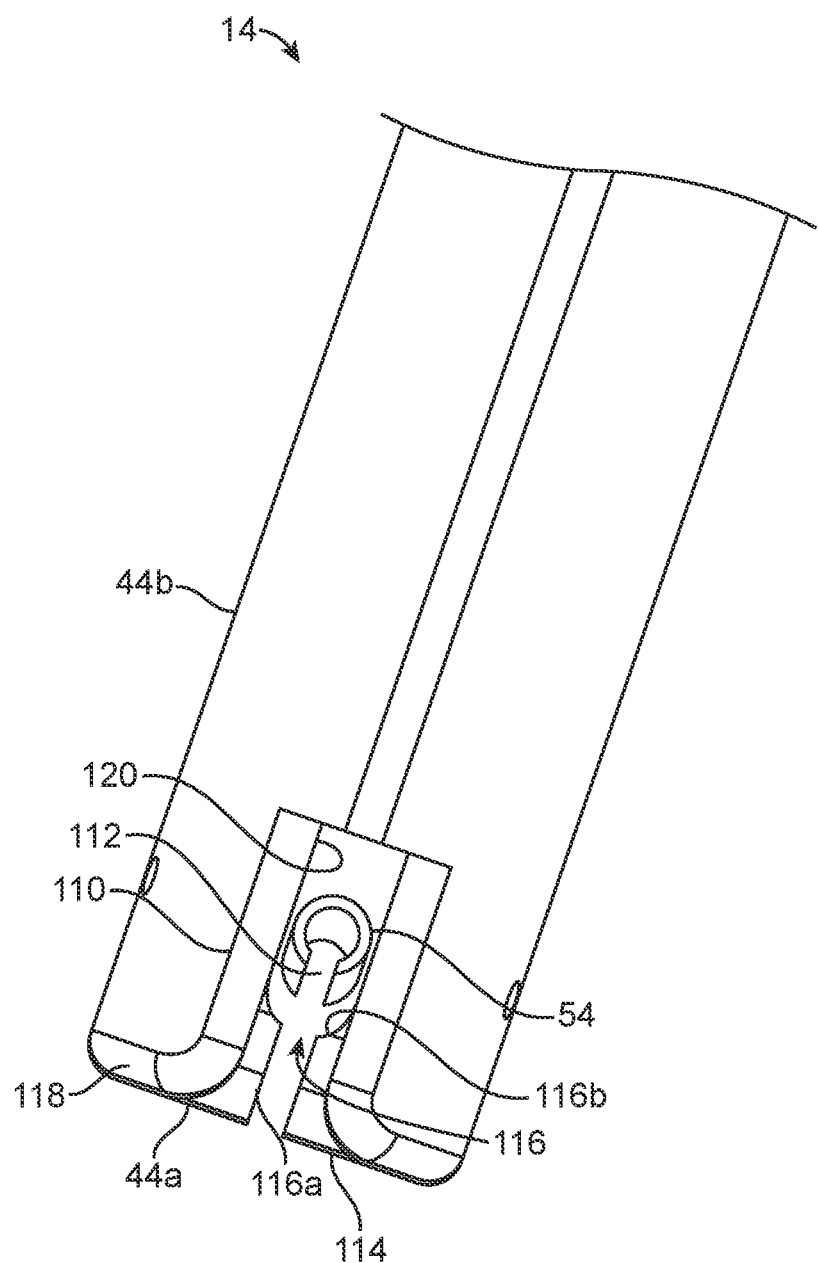
FIG. 16 is a top, close-up, view of the distal end of the laparoscopic suture passer of FIG. 2, particularly showing the jaw members in the closed position, and the needle in the deployed position.
Figure 17:
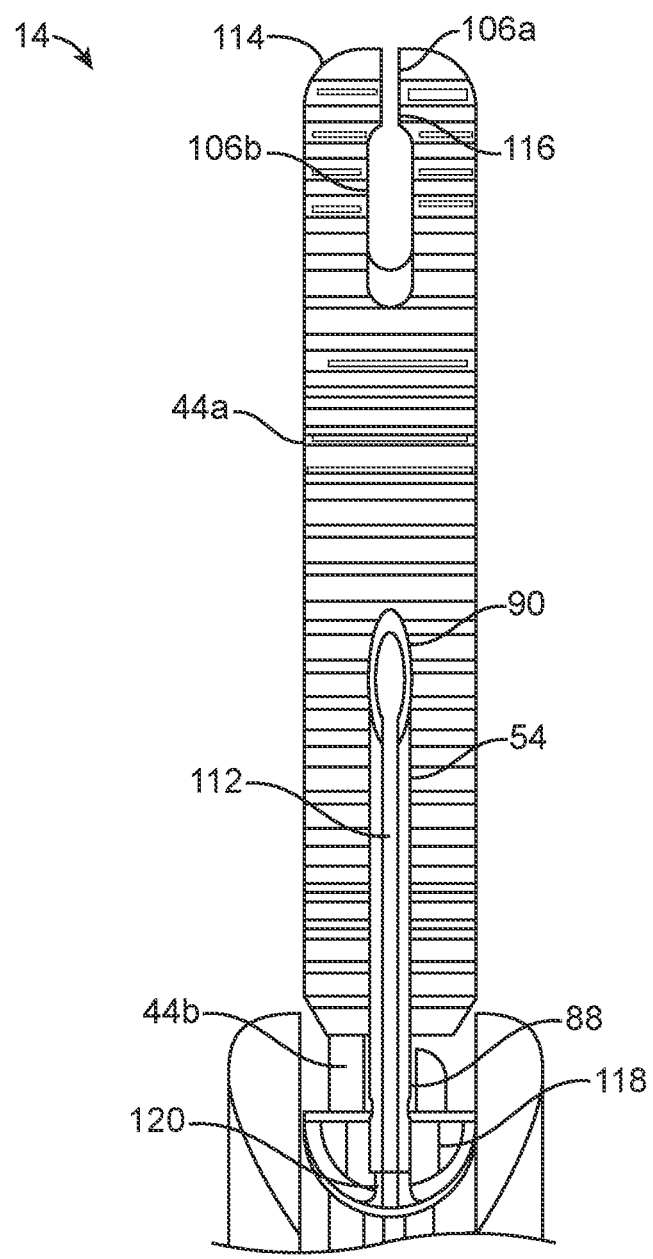
FIG. 17 an axial, close-up, view of the distal end of the laparoscopic suture passer of FIG. 2, particularly showing the jaw members in the open position, and the needle in the deployed position.
Figure 18:
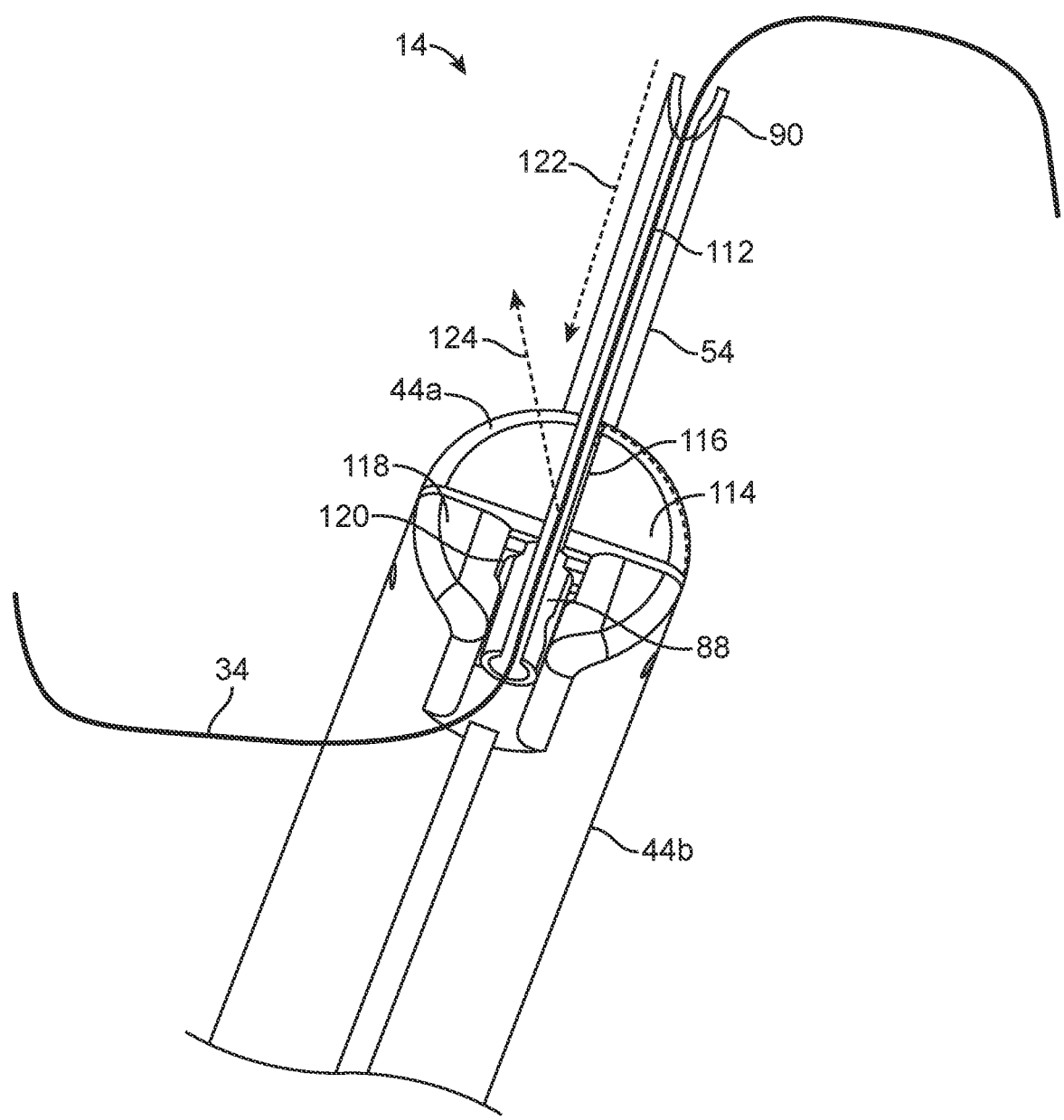
FIG. 18 is a perspective, close-up, view of the distal end of the laparoscopic suture passer of FIG. 2, particularly showing the jaw members in the closed position, and the needle in the deployed position.

In particular, as best illustrated in FIGS. 16-18 (push-pull wire 100 not shown for purposes of clarity), the needle 54 comprises a slotted bore 112 extending along the entire longitudinal axis 98 (i.e., length) of the needle 54. In the illustrated embodiment, the slotted bore 112 faces distally when the needle 54 is in the deployed position (FIGS. 17 and 18). As best shown in FIGS. 7 and 17, the upper jaw member 44a comprises a cleaved distal tip 114 that forms an open slot 116 having a narrow slot portion 116a and a wide slot portion 116b, while the lower jaw member 44b comprises a cleaved distal tip 118 that forms an open slot 120. The wide slot portion 116b of the upper jaw member 42a allows the sharp end 90 of the needle 54 to traverse the lower jaw member 44b, and in particular allows the sharp end 90 of the needle 54 to pass through the cleaved distal tip 114 of the upper jaw member 44a when the jaw members 44a, 44b are displaced relative to each other from the open position (FIG. 17) into the closed position (FIG. 18). In this manner, the upper jaw member 44a will not mechanically interfere with the needle 54 as it passes through tissue that is grasped between the jaw members 44a, 44b. As illustrated in FIGS. 7, 17 and 18, the open slot 120 of the lower jaw member 44b accommodates the blunt end 88 of the needle 54 when the needle 54 is in the deployed position.

The respective open slots 116, 120 in the cleaved distal tips 114, 118 of the jaw members 44a, 44b communicate with the distally facing slotted bore 112 of the needle 54. For example, it can be seen from FIGS. 7 and 18 that the open slots 116, 120 of the jaw members 42, 44b create a contiguous slot that communicates with the slotted bore 112 of the needle 54. Thus, when the jaw members 44a, 44b are in any position between the closed position and the open position, a suture 34 that is axially threaded through the slotted bore 112 of the needle 54 (shown by the arrow 122) may be laterally removed from the slotted bore 112 and out of the open slots 116, 120 (shown by the arrow 124), thereby decoupling the suture 34 from the laparoscopic suture passer 14.

Thus, it can be appreciated from the foregoing that laparoscopic suture grasper 12, while the jaw members 44a, 44b are in the closed position, with the needle 54 in the retracted position (see FIG. 2), may be introduced through a laparoscopic port into the patient adjacent tissue to be sutured; the jaw members 44a, 44b displaced relative to each other from the closed position to the open position (see FIG. 3) via manipulation of the pivotable handle piece 50; the needle 54 displaced from the retracted position to the deployed position (see FIG. 4) via manipulator of the slider mechanism 60; and the jaw members 44a, 44b displaced toward each other from the open position to the open position, while the needle 54 is in the deployed position (see FIG. 5) to grasp the tissue between the jaw members 44a, 44b while passing the deployed needle 54 through the cleaved distal tip 114 of the upper jaw member 24 and through the tissue. The suture 34 may then be threaded through the needle 54 to stitch the tissue; the jaw members 44a, 44b displaced away from each other towards the open position to release the tissue therebetween; and suture 34 laterally removed out of the slotted bore 112 and open slots 108 and 112 of the jaw members 44a, 44b to decouple the suture 34 from the laparoscopic suture grasper 12 (see FIG. 18). Additional stiches can be made in the tissue, and once completed, the needle 54 may be displaced from the deployed position to the retracted position (see FIG. 3) via manipulator of the slider mechanism 60; the jaw members 44a, 44b displaced relative to each other from the open position to the closed position (see FIG. 2) via manipulation of the pivotable handle piece 50; and the laparoscopic suture passer 16 removed from the patient introduced through the laparoscopic port.

Referring to FIGS. 19-27, an alternative embodiment of a laparoscopic suture passer 14' will now be described. The laparoscopic suture passer 14' is similar to the laparoscopic suture passer 14 illustrated in FIGS. 2-18, with the exception that the laparoscopic suture passer 14' comprises a needle 54' having a funnel-shaped end 88'. The funnel-shaped end 88' has a base 130 and a neck 132. The base 130 narrows to the neck 132 as it progresses towards the sharp end 90 of the needle 54', such that the funnel-shaped end 88' facilitates axial threading of the suture 34 through a slotted bore 112' of the needle 54' when the suture 34 is inserted into the base 130 of the funnel-shaped end 88'.

Figure 25:
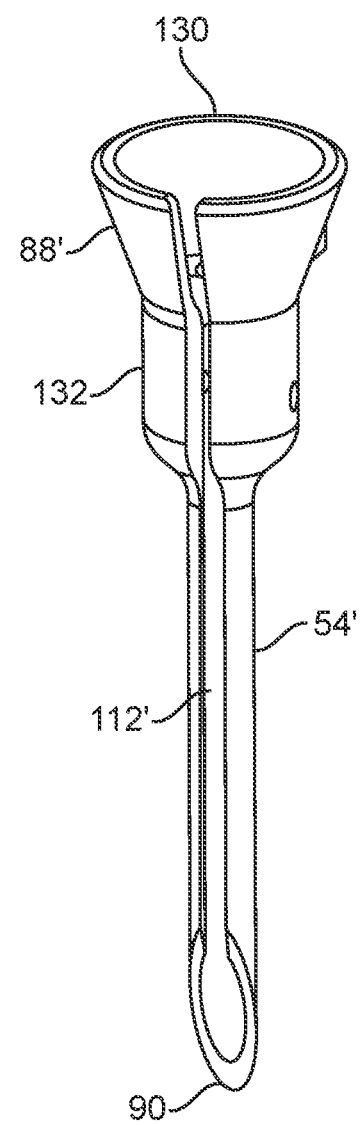
FIG. 25 is another close-up profile view of the needle used in the laparoscopic suture passer of FIG. 19.
Figure 26:
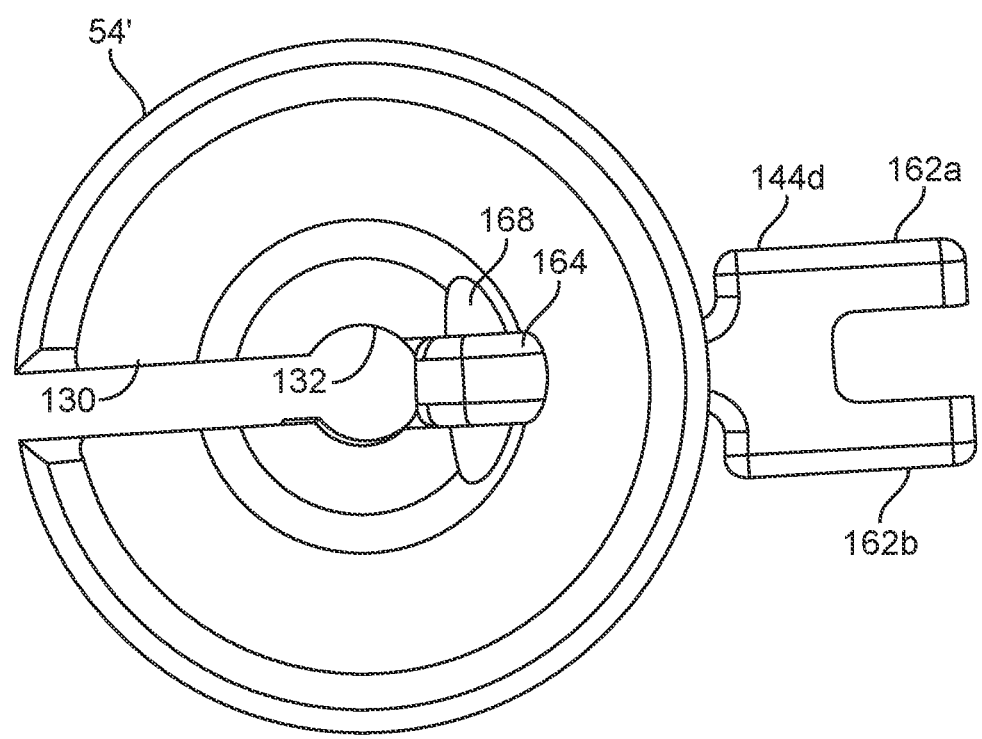
FIG. 26 is another close-up top view of the needle used in the laparoscopic suture passer of FIG. 19.
Figure 27:
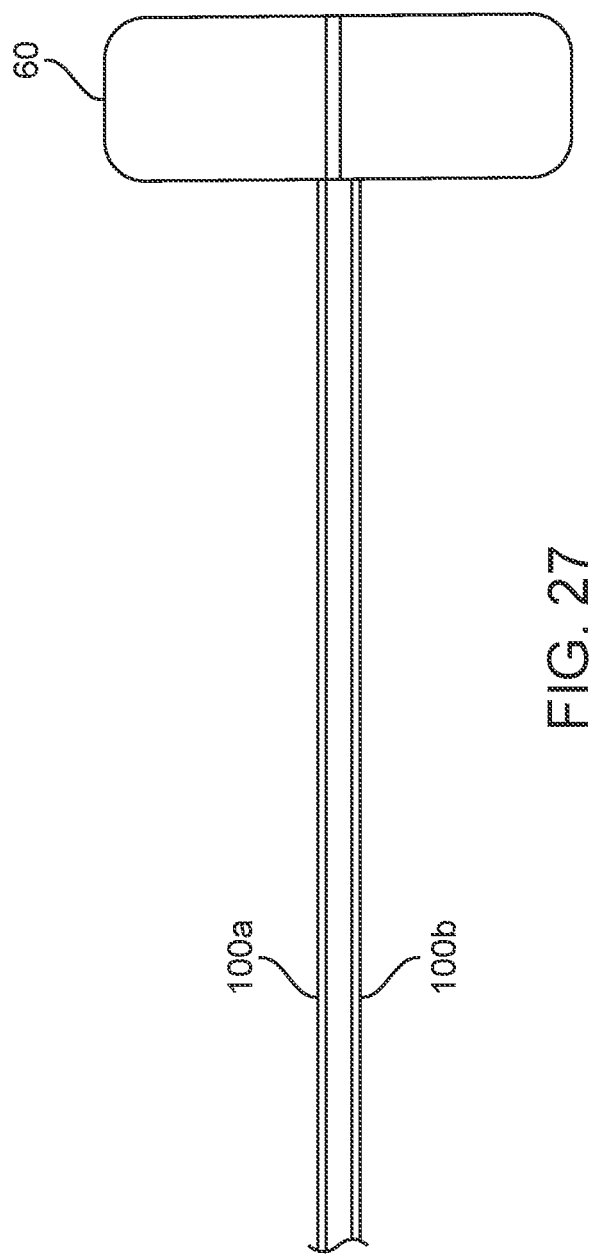
FIG. 27 is a profile of a slider mechanism coupled to proximal push-pull wires of the linkage mechanism of FIG. 23.

As best illustrated in FIGS. 25 and 26, the slotted bore 112' extends entirely through the length of the needle 54', including the funnel-shaped end 88'. The slotted bore 112' faces distally when the needle 54 is in the deployed position in the same manner as the slotted bore 112 of the needle 54 of the laparoscopic suture passer 14 when in the deployed position (FIGS. 17 and 18). The distally facing slotted bore 112' of the needle 54' communicates with open slots 116', 120' in cleaved distal tips 114', 118' of jaw members 44a', 44b' in the same manner as the distally facing slotted bore 112 of the needle 54 communicates with the open slots 116, 120 in the cleaved distal tips 114, 118 of the jaw members 44a, 44b (shown in FIG. 18), such that a suture 34 that is axially threaded through the slotted bore 112' of the needle 54' may be laterally removed from the slotted bore 112' and out of the open slots 116', 120', thereby decoupling the suture 34 from the laparoscopic suture passer 14'. The funnel-shaped end 88' of the needle 54' is hingedly coupled to the lower jaw member 44b' via a pivot pin 92', such that the needle 54' may be alternately hinged between a retracted position and a deployed position in the same manner as the needle 54 of the laparoscopic suture passer 14 is alternately hinged between the retracted position (see FIG. 13) and the deployed position (see FIG. 14).

The laparoscopic suture passer 14' also differs from the laparoscopic suture passer 14 illustrated in FIGS. 2-18 in that one of the jaw members 44a', 44b' of the laparoscopic suture passer 14' is immovably affixed to the distal end 40 of the shaft 36, while the other of the jaw members 44a', 44b' is pivotably affixed to the distal end 40 of the shaft 36. In the illustrated embodiment, the lower jaw member 44b is immovably affixed to the distal end 40 of the shaft 36, while the upper jaw member 44a is pivotably affixed to the distal end 40 of the shaft 36, although in another embodiment, the upper jaw member 44a may be immovably affixed to the distal end 40 of the shaft 36, while the lower jaw member 44b may be pivotably affixed to the distal end 40 of the shaft 36.

Although displacement of the jaw members 44a', 44b' of the laparoscopic suture passer 14' relative to each other is not as large as the displacement of the jaw members 44a, 44b of the laparoscopic suture passer 14 relative to each other, the upper jaw member 44a of the laparoscopic suture passer 14' comprises an extended open slot 118' (as best illustrated in FIG. 21) that allows the needle 54' to pass therethrough when displaced from the retracted position into the deployed position. In the preferred embodiment, the needle 54' may pass through the open slot 118' of the upper jaw member 44a even when the jaw members 44a', 44b' are in the closed position.

As best illustrated in FIGS. 19, 20, and 22, the laparoscopic suture passer 14' comprises a linkage 58' between the pivotable finger piece 50 and the upper jaw member 44a. The linkage 58' comprises the generally cylindrical reciprocating rod 66 (described above with respect to the laparoscopic suture passer 14) that resides within a main central lumen (not shown) extending through the shaft 36, a flattened rigid link 72a' operatively associated with the reciprocating rod 66, and a flattened rigid link 74a' respectively integrated with the upper jaw member 44a'. In the illustrated embodiment, the rigid link 72a' is pivotably coupled to the flattened distal end 70 of the reciprocating rod 66. The proximal end of the lower jaw member 44b' has a flattened flange 74b' that is immovably affixed to the distal end 40 of the shaft 36. The distal parallel arms 76 of the shaft 36 support the rigid link 74a' integrated with the upper jaw member 44a', the flattened flange 74b' of the lower jaw member 44b', and the rigid link 72a' operably associated with the reciprocating rod 66.

In particular, the flattened flange 74b' of the lower jaw member 44b' is affixed to one of the distal parallel arms 76 via two rivets 134 (shown in FIG. 22), such that the lower jaw member 44b' is incapable of moving relative to the distal end 40 of the shaft 36, and the rigid link 74a' integrated with the upper jaw member 44a' is pivotably coupled between the distal parallel arms 76 of the shaft 36 via a single pivot pin 78' (shown in FIG. 20). The rigid link 72a' is pivotably coupled between the distal end 70 of the reciprocating rod 66 and the rigid link 74a' respectively via a single pivot pin 80' and a single pivot pin 82' (shown best in FIG. 22).

In the same manner described above with respect to the linkage 58, the linkage 58' comprises a boss 84 affixed to the proximal end 68 of the reciprocating rod 66 in an interference relationship with the pivotable finger piece 50, as illustrated in FIG. 1. Thus, displacement of the reciprocating rod 66 in the distal direction 74 in response to displacing the pivotable finger piece 50 towards the handle 48 (shown by the arrow 52a in FIG. 1), causes the rigid links 72a', 74a' to pivot outwards away from the distal end 40 of the shaft 36, thereby displacing the upper jaw member 44a' away from the fixed lower jaw member 44b' to the open position, as best shown in FIG. 19. Conversely, displacement of the reciprocating rod 66 in the proximal direction 72 in response to displacing the pivotable finger piece 50 away from handle 48 (shown by the arrow 52b in FIG. 1), causes the rigid links 72a', 74a' to pivot inwards toward the distal end 40 of the shaft 36, causing the upper jaw member 44a' to be displaced toward the fixed lower jaw member 44b' to the closed position.

The laparoscopic suture passer 14' lastly differs from the laparoscopic suture passer 14 illustrated in FIGS. 2-18 in that laparoscopic suture passer 14' includes an anti-buckling linkage assembly 136. In particular, as illustrated in FIGS. 19-23, the linkage assembly 136 comprises a sleeve 138 slidably disposed relative to the shaft 36, two diametrically opposed proximal push-pull wires 100a, 100b coupled to a proximal end 140 of the sleeve 138 via respective connectors 144a, 144b, and a distal push-pull wire 100c coupled between a distal end 142 of the sleeve 138 via a connector 144c and the funnel-shaped end 88' of the needle 54' via a connector 144d. In the illustrated embodiment, the sleeve 138 is generally cylindrically shaped and comprises a sidewall opening 146 through which rigid links 72a', 74a' pivot outwards away from the distal end 40 of the shaft 36 when the upper jaw member 44a' is displaced away from the fixed lower jaw member 44b' to the open position, as best shown in FIG. 19, and through which the links 72a', 74a' pivot inwards toward the distal end 40 of the shaft 36 when the upper jaw member 44a' is displaced toward the fixed lower jaw member 44b' to the closed position.

The distal push-pull wire 100c extends from the funnel-shaped end 88' of the needle 54' in the proximal direction to the sleeve 138 along an open pull wire channel 108' (shown in FIG. 20) that longitudinally runs along the bottom surface of the lower jaw member 44b, while the proximal push-pull wires 100a, 100b extend from the slider mechanism 60 (shown in FIG. 27) in the distal direction to the sleeve 138 along open pull wire channels 110' (one shown in FIG. 22) that longitudinally run along the diametrically opposed surfaces of the rod 66. Alternatively, instead of running along the open pull wire channels 110', the proximal push-pull wires 100a, 100b may be slidably disposed through wire lumens (not shown) that longitudinally extend through the shaft 36 separately from the central lumen 76 of the shaft 36. In the illustrated embodiment, the proximal push-pull wires 100a, 100b and distal push-pull wire 100c are flattened, and the wire channels 108', 110' are rectangular, such that the push-pull wires 100a-100c conform to and are guided within the wire channels 108', 110'. Thus, it can be appreciated that the wire channels 108', 110' (or alternatively the pull wire lumens) provide support to the push-pull wires 100a-100c, thereby further ensuring that the push-pull wires 100a-100c do not axially buckle when displaced in the distal direction.

Figure 23:
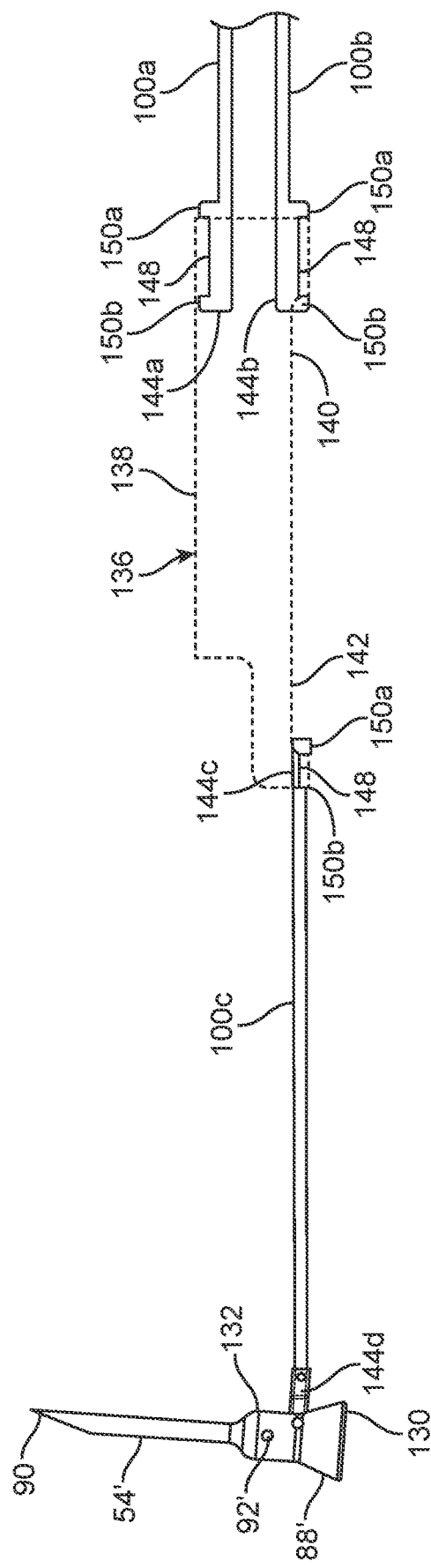
FIG. 23 is a profile view of a linkage mechanism used to displace the needle of the laparoscopic suture passer of FIG. 19 between a deployed position and a retracted position.
Figure 24:
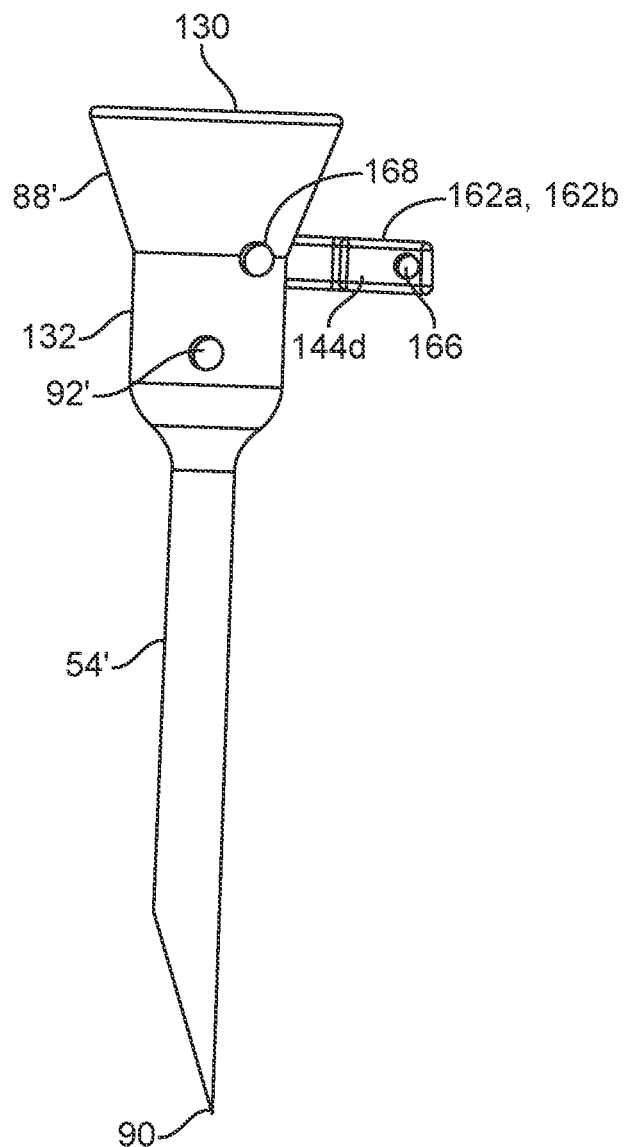
FIG. 24 is a close-up profile view of the needle used in the laparoscopic suture passer of FIG. 19.

As best shown in FIG. 23, each connector 144a, 144b that couples a respective proximal push-pull wire 100a, 100b to the proximal end 140 of the sleeve 138 comprises a recess 148 flanked by two ridges 150a, 150b. Diametrically opposed proximal portions of the sleeve 138 respectively fit within the recesses 148 of the diametrically opposed connectors 144a, 144b. In particular, as best shown in FIG. 21, the two ridges 150a, 150b of the connector 144a respectively engage a proximal-most edge 152 of the sleeve 138 and a small sidewall opening 156 in the sleeve 138, such that the connector 142a is interference fit with the sleeve 138. As best shown in FIG. 20, the two ridges 150a, 150b of the connector 144b respectively engage the proximal-most edge 152 of the sleeve 138 and a proximal-most edge 154 of the sidewall opening 146, such that the connector 144b is interference fit with the sleeve 138.

Likewise, the connector 144c that couples the distal push-pull wire 100c to the distal end 142 of the sleeve 138 comprises a recess 148 flanked by two ridges 150a, 150b. The distal portion of the sleeve 138 fits within the recess 148 of the connector 144c. In particular, as best shown in FIG. 20, the two ridges 150a, 150b of the connector 144c respectively engage a distal-most edge 158 of the sleeve 138 and a distal-most edge 160 of the sidewall opening 146, such that the connector 142c is interference fit with the sleeve 138.

As best shown in FIG. 26, the connector 144d is T-shaped comprising two parallel members 162a, 162b and a base member 164. The distal end of the distal push-pull wire 100c is affixed between the parallel members 162a, 162b of the connector 144d via a pin 166, and the funnel-shaped end 88' of the needle 54' includes a through-hole 168 through which the base member 164 of the connector 144d extends and coupled via a pin (not shown).

Figure 28:
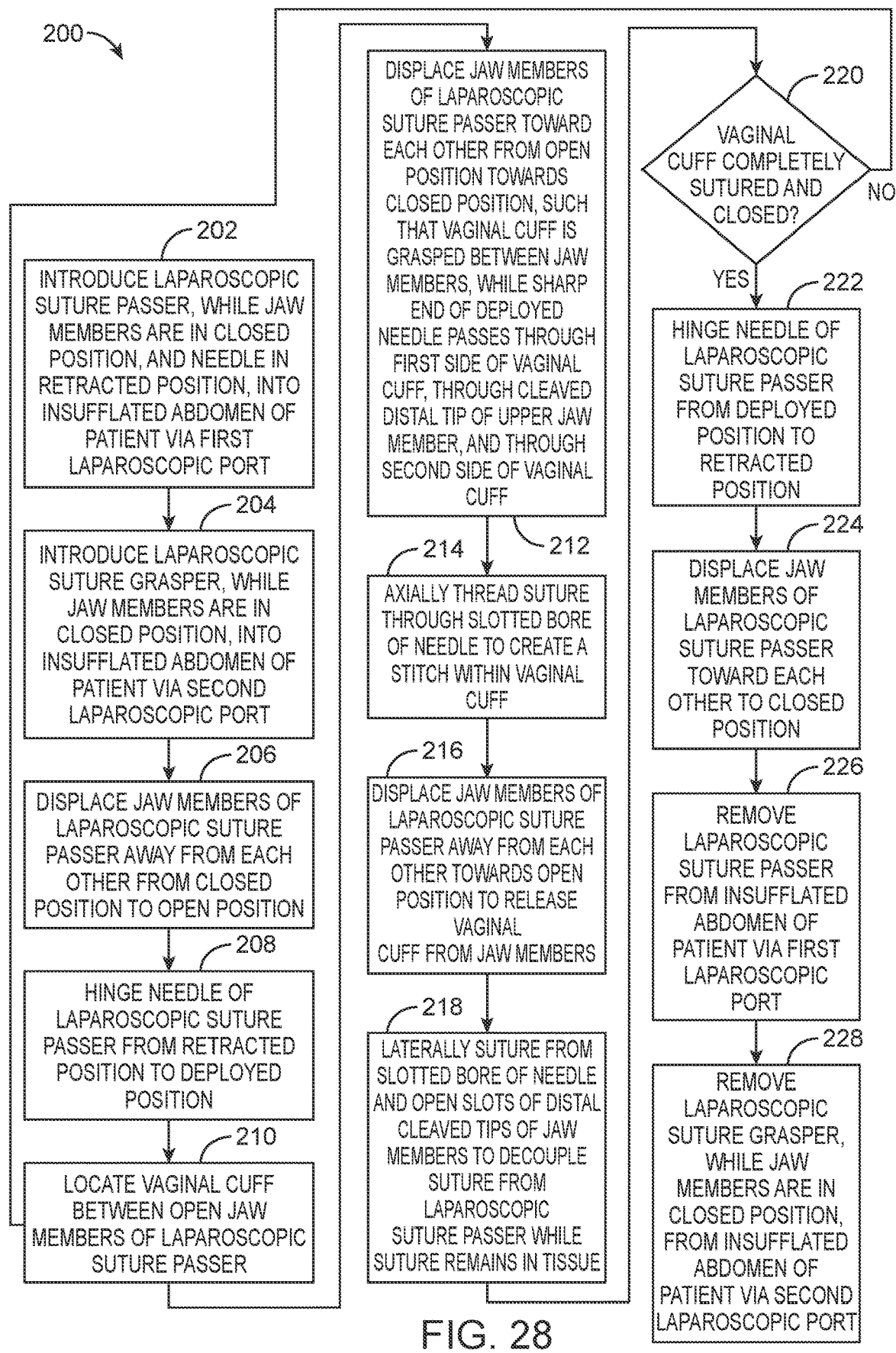
FIG. 28 is a flow diagram illustrating one exemplary method of operating the laparoscopic suturing system of FIG. 1 to perform a post-total laparoscopic hysterectomy (TLH) suturing procedure on a vaginal cuff of a patient.
Figure 29F:
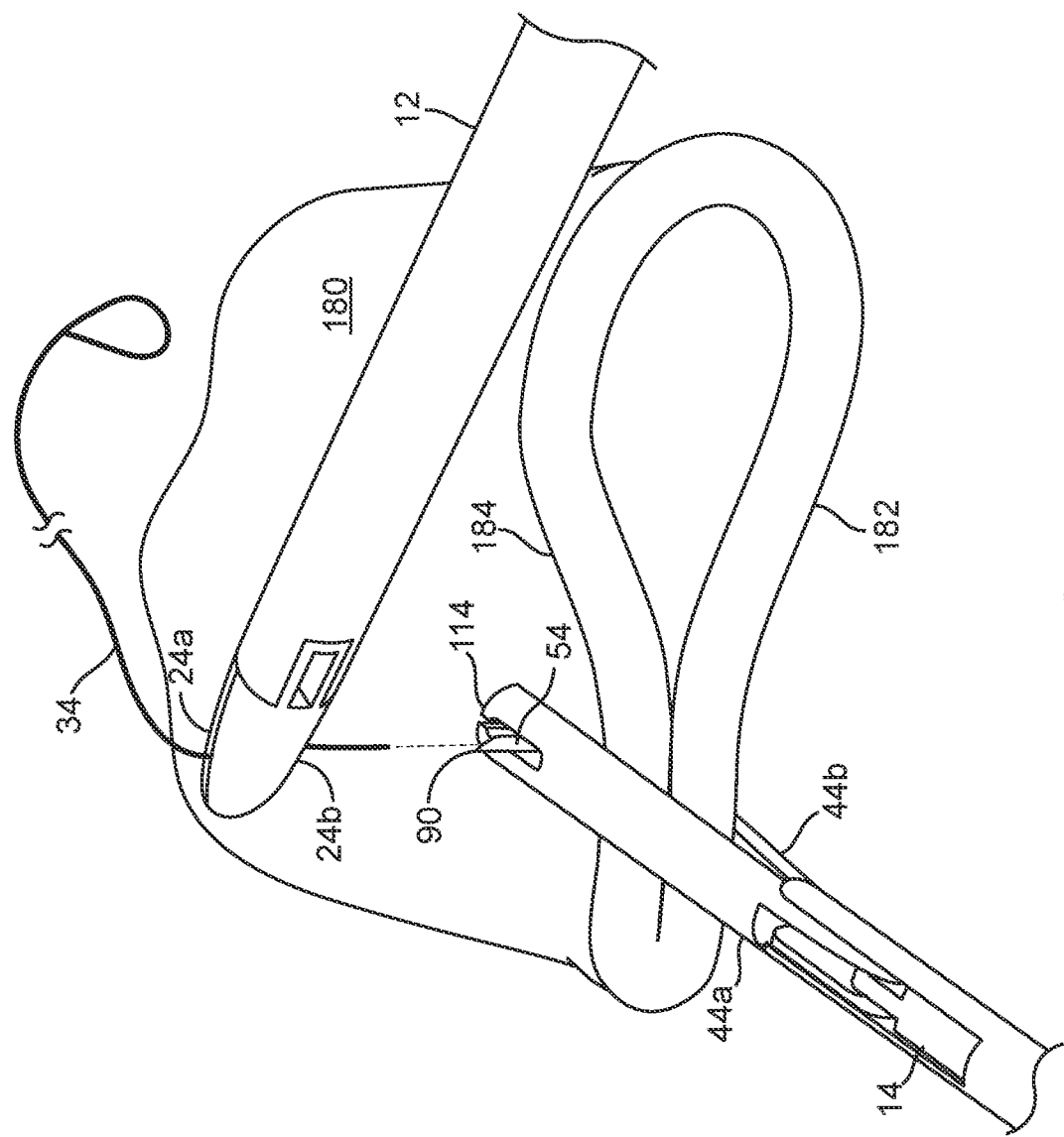
FIGS. 29A-29P are plan views illustrating the method of FIG. 28.
Figure 29G:
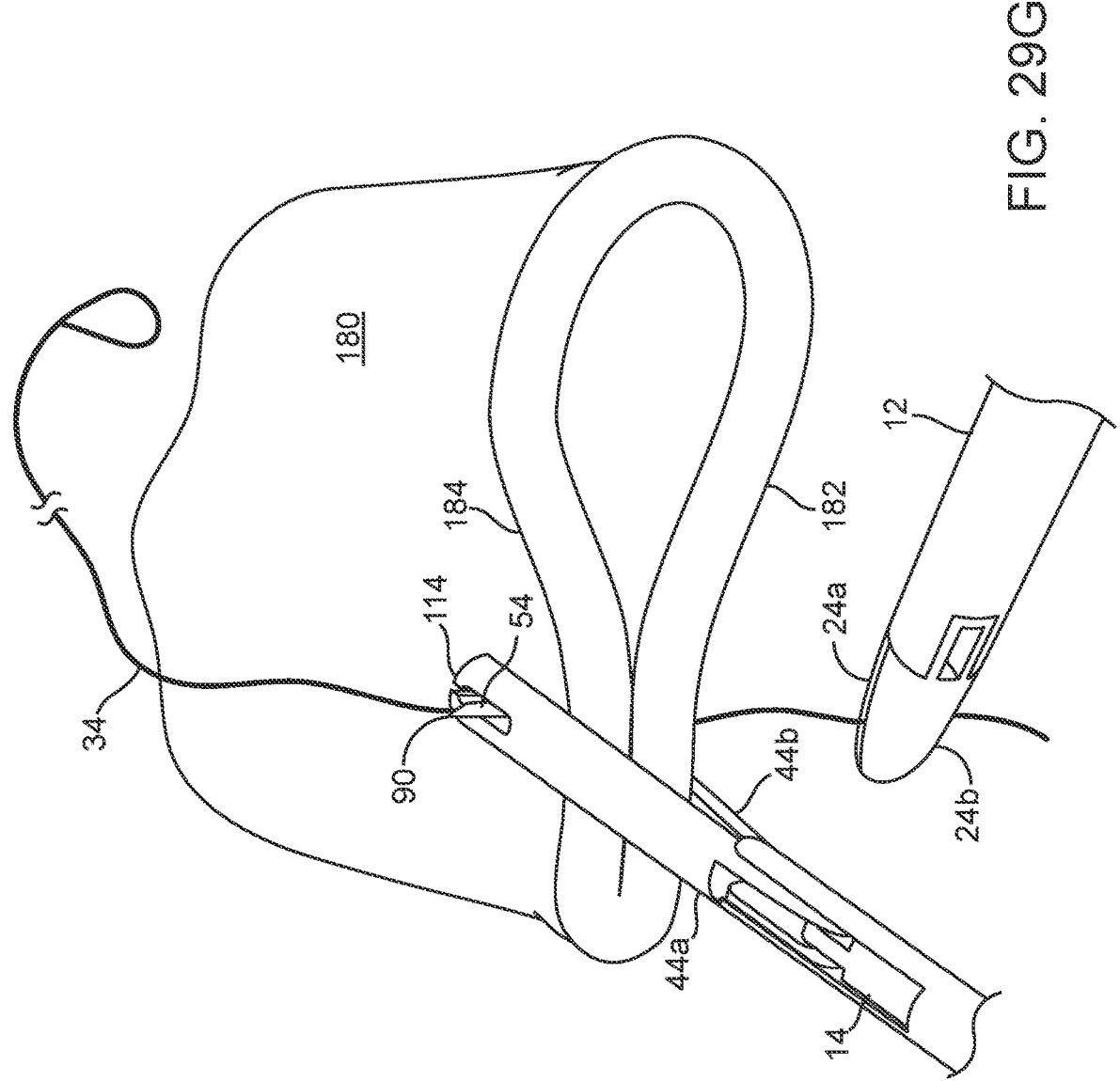
Figure 29H:
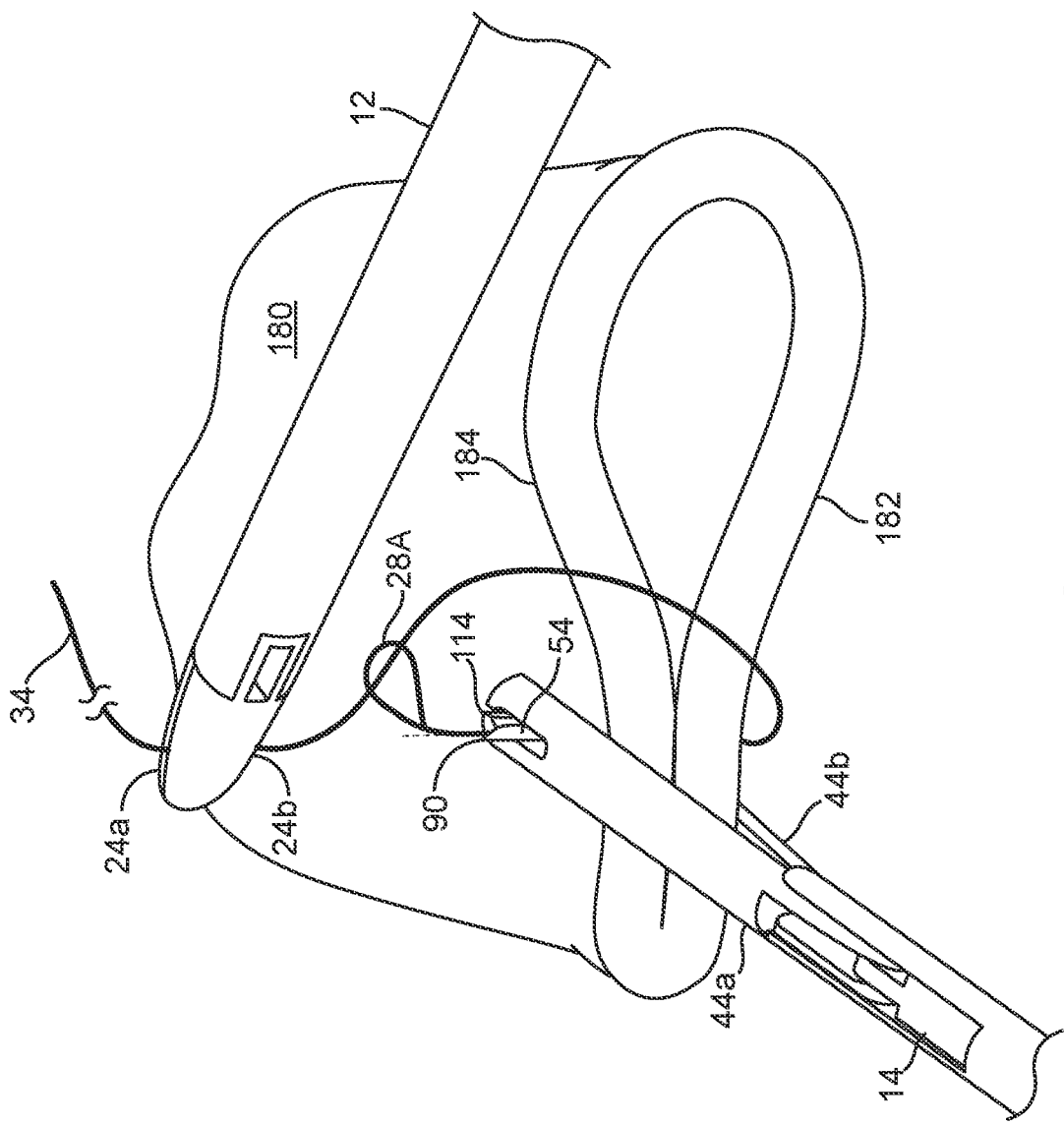
Figure 29I:
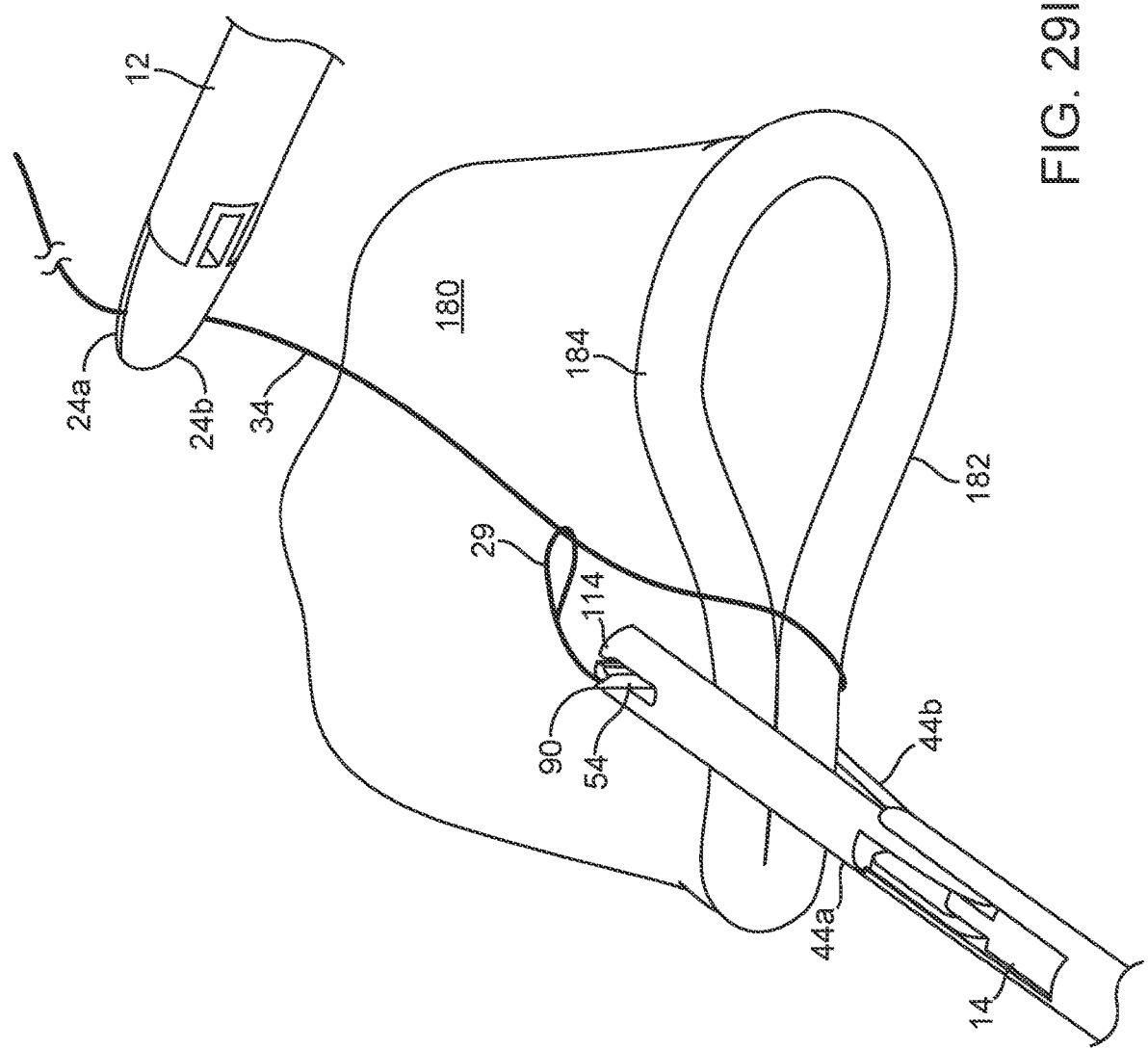
Figure 29J:
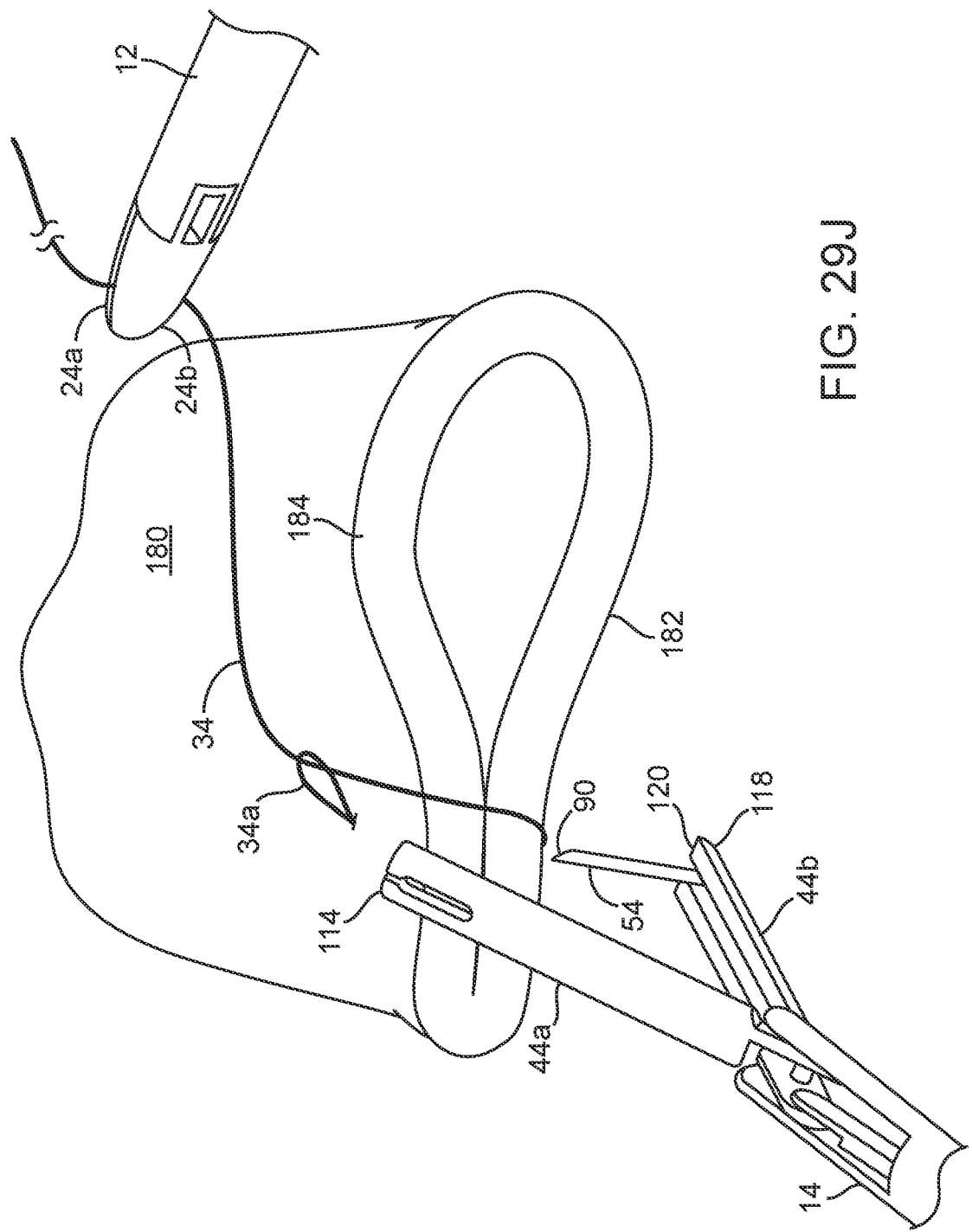
Figure 29K:
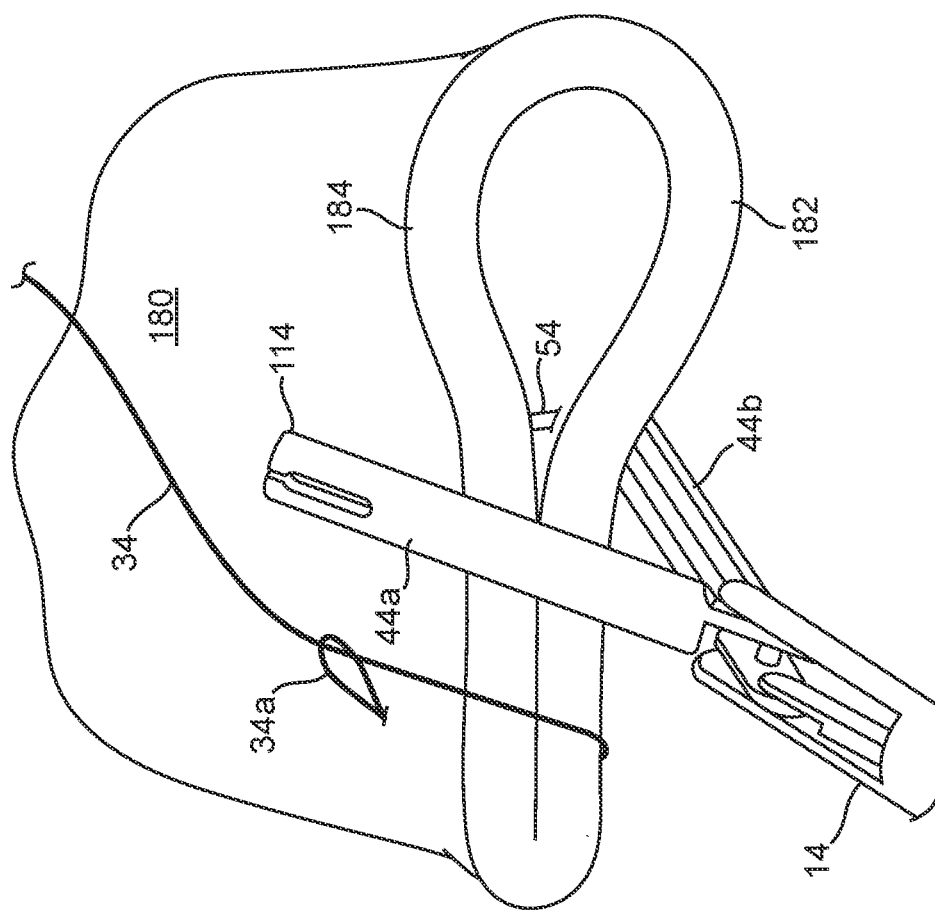
Figure 29L:
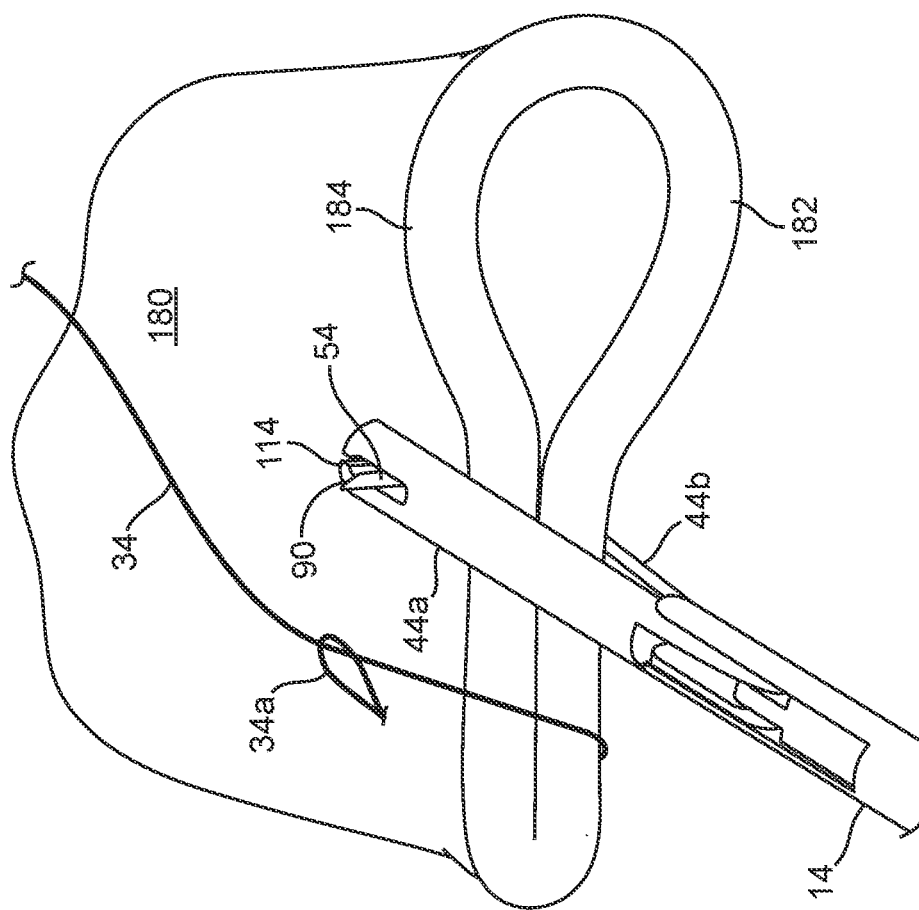
Figure 29M:
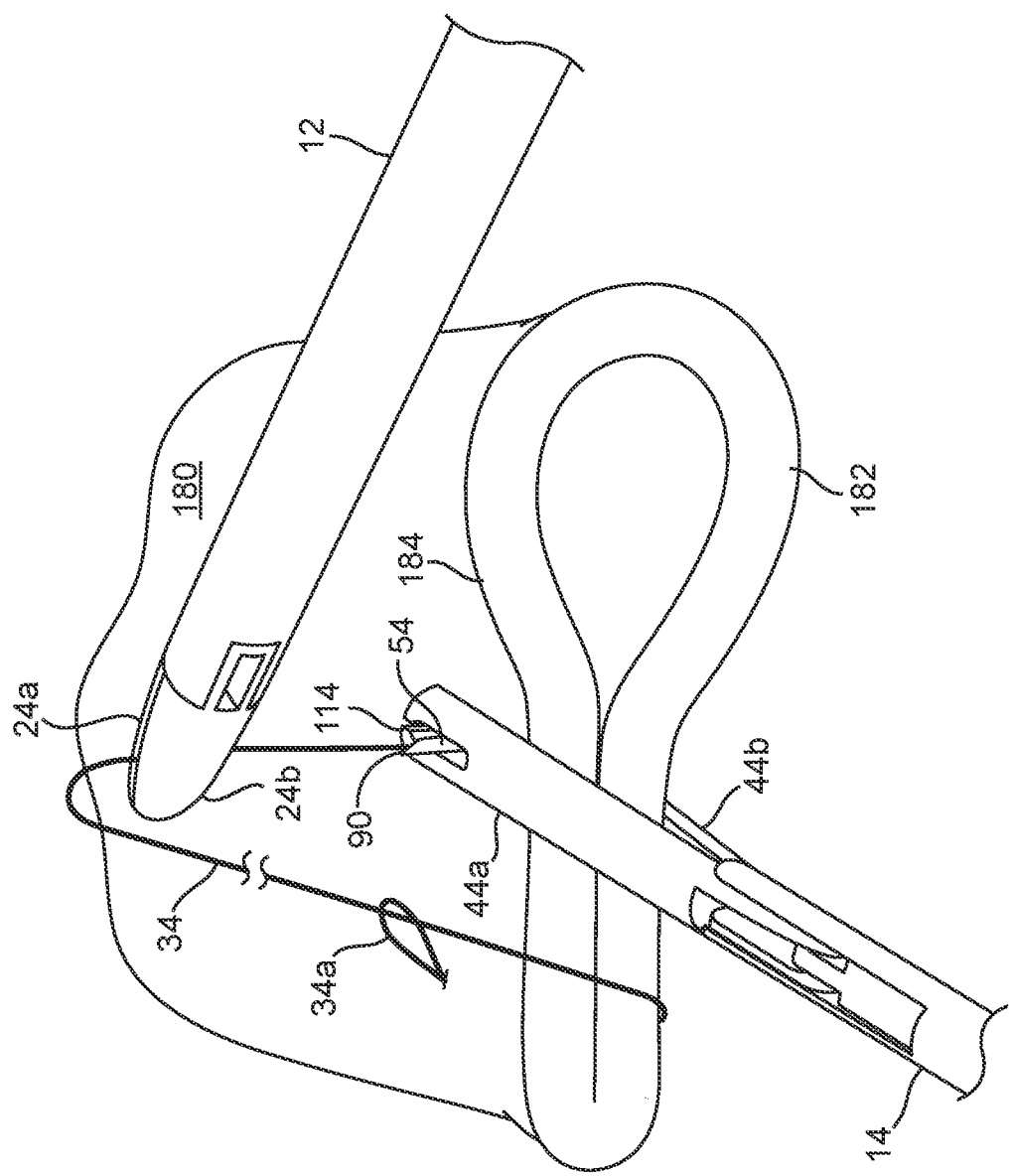
Figure 29N:
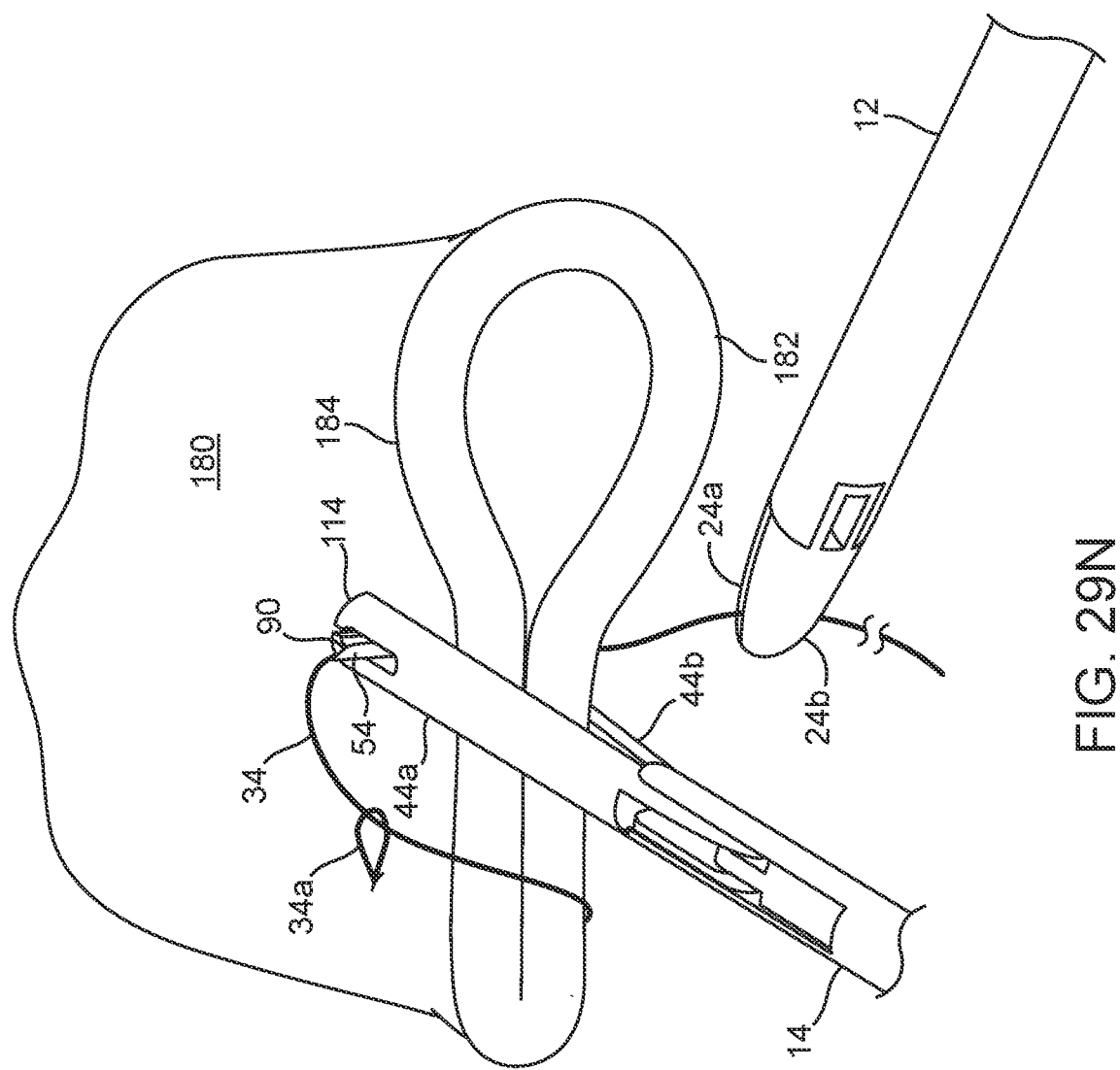

Referring to FIGS. 28 and 29A-29N, one exemplary method 200 of using the laparoscopic suturing system 10 to perform a post-total laparoscopic hysterectomy (TLH) vaginal cuff suturing procedure on a patient will now be described. It is assumed that the uterus of the patient has been removed (either though a transvaginal hysterectomy or laparoscopic hysterectomy), leaving behind an open vaginal cuff 180 that requires suturing. The method 200 will be described with respect to the laparoscopic suture passer 14 of FIGS. 2-18, although it should be appreciated the laparoscopic suture passer 14' of FIG. 19-27 may be used to achieve equivalent results.

First, the laparoscopic suture grasper 12, while the jaw members 24a, 24b are in the closed position and grasping a suture 34, is introduced through a first conventional laparoscopic port into the insufflated abdomen of the patient (step 202), and the laparoscopic suture passer 14, while the jaw members 44a, 44b are in the closed position and the needle 54 is in the retracted position (see FIG. 29A), is introduced through a second conventional laparoscopic port into the insufflated abdomen of the patient (step 204). It should be appreciated that laparoscopic grasping instrument 12 may be introduced into the insufflated abdomen of the patient before or after the introduction of the laparoscopic suture passer 14.

Next, the jaw members 44a, 44b of the laparoscopic suture passer 14 are displaced away from each other from the closed position to the open position (see FIG. 29B) via manipulation of the finger piece 50 (shown in FIG. 1) (step 206), and the needle 54 is hinged from the retracted position to the deployed position (see FIG. 29C) via manipulation of the slider mechanism 60 (shown in FIG. 1) (step 208).

Next, the vaginal cuff 180 is located between the open jaw members 44a, 44b of the laparoscopic suture passer 14 (see FIG. 29D) (step 210), and the jaw members 44a, 44b of the laparoscopic suture passer 14 are displaced toward each other from the open position to the closed position via manipulation of the finger piece 50 (shown in FIG. 1), such that the vaginal cuff 180 is grasped between the jaw members 42, 44b, while the sharp end 90 of the needle 54 passes through a first side 182 of the vaginal cuff 180, through the cleaved distal tip 114 of the upper jaw member 44a, and through the second side 184 of the vaginal cuff 180 (see FIG. 29E) (step 212).

Next, the suture 34 is axially threaded through the slotted bore 112 (shown in FIG. 18) of the needle 54 via operation of the laparoscopic suture grasper 12 to create a stitch (step 214). For example, via manipulation of the laparoscopic suture grasper 12, the end of the suture 34 may be inserted into the sharp end 90 of the needle 54 (see FIG. 29F), axially pushed through the slotted bore 112 of the needle 54 on the second side 184 of the vaginal cuff 180 until the distal end of the suture 34 passes out of the blunt end 88 (not shown) of the needle 54 (and thus out of the first side 182 of the vaginal cuff 180), and then axially pulled through the slotted bore 112 of the needle 54 from the first side 182 of the vaginal cuff 180 (see FIG. 29G) until the looped end 34a of the suture 34 abuts the sharp end 90 of the needle 54 at the first side 182 of the vaginal cuff 180. The end of the suture 34 may then be threaded through the looped end 34a of the suture 34 (see FIG. 29H), and tightened to form a stitch (see FIG. 29I). Alternatively, via manipulation of the laparoscopic suture grasper 12, the end of the suture 34 may be inserted into the blunt end 88 of the needle 54, axially pushed through the slotted bore 112 (not shown) of the needle 54 on the first side 182 of the vaginal cuff 180 until the distal end of the suture 34 passes out of the sharp end 90 of the needle 54 (and thus out of the second side 184 of the vaginal cuff 180), and then axially pulled through the slotted bore 112 of the needle 54 from the second side 184 of the vaginal cuff 180 (see FIG. 29G) until the looped end 34a of the suture 34 abuts the sharp end 90 of the needle 54 on first side 182 of the vaginal cuff 180.

Once the stitch is created, the jaw members 44a, 44b of the laparoscopic suture passer 14 are displaced away from each other towards the open position via manipulation of the finger piece 50 (shown in FIG. 1) to release the vaginal cuff 180 (step 216), and the suture 34 is laterally removed through the slotted bore 112 (not shown) of the needle 54 and through the open slots 116, 120 of the jaw members 44a, 44b to mechanically decouple the laparoscopic suture passer 14 from the suture 34 (step 218) (see FIG. 29J).

Figure 29O:
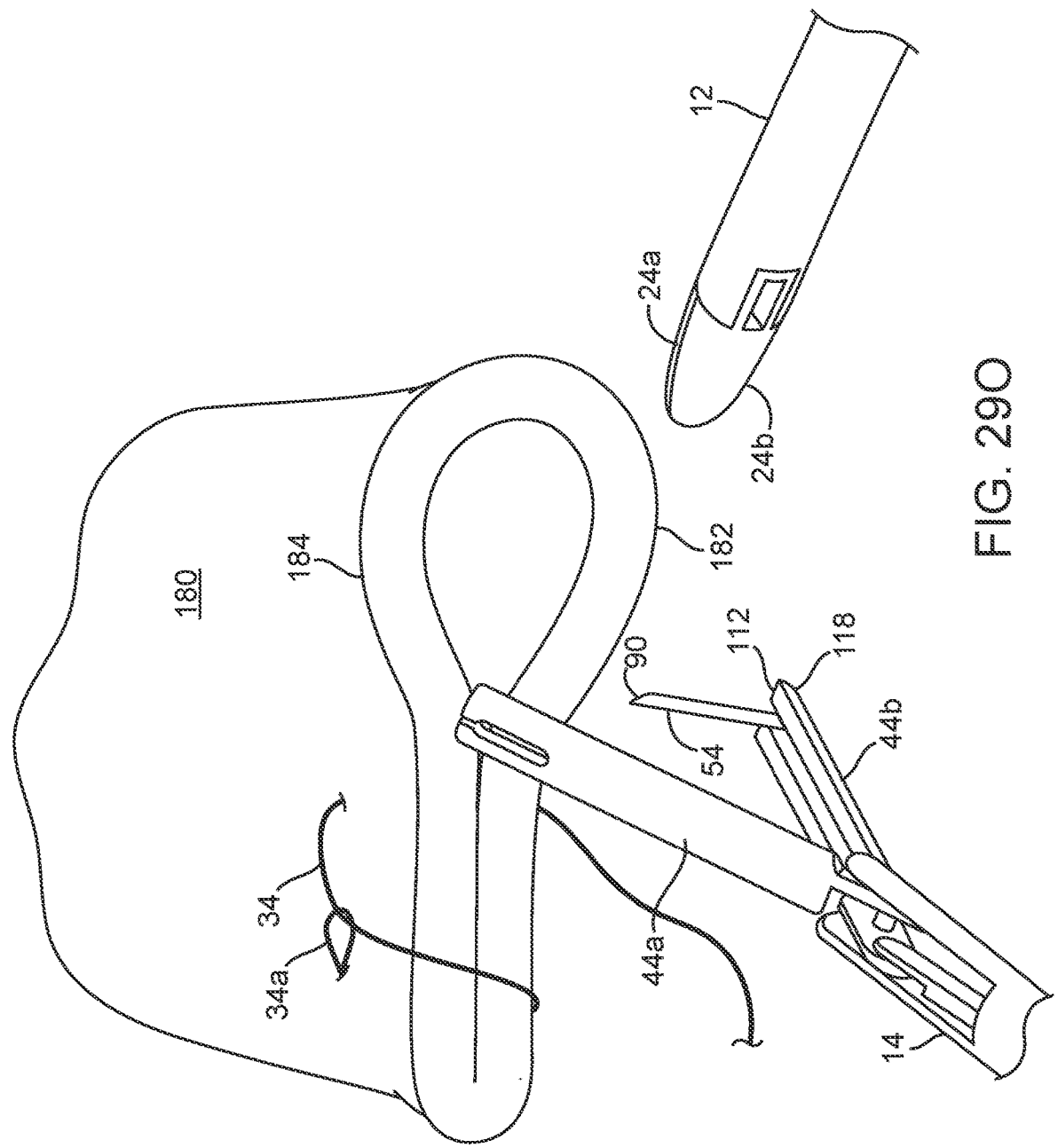

Next, as long as the vaginal cuff 180 is not completely sutured and closed (step 220), steps 210-218 are repeated to create additional stitches in the vaginal cuff 180. For example, another portion of the vaginal cuff 180 may be located between the open jaw members 44a, 44b of the laparoscopic suture passer 14 (see FIG. 29K), the jaw members 44a, 44b of the laparoscopic suture passer 14 displaced toward each other from the open position to the closed position via manipulation of the finger piece 50 (shown in FIG. 1), such that the sharp end 90 of the needle 54 passes through the first side 182 of the vaginal cuff 180, through the cleaved distal tip 114 of the upper jaw member 44a, and through the second side 184 of the vaginal cuff 180 (see FIG. 29L), the suture 34 axially threaded through the needle 54 via operation of the laparoscopic suture grasper 12 (see FIG. 29M), and tightened to form another stitch (see FIG. 29N), the jaw members 44a, 44b of the laparoscopic suture passer 14 displaced away from each other towards the open position via manipulation of the finger piece 50 (shown in FIG. 1) to release the vaginal cuff 180, and the suture 34 laterally removed through the slotted bore 112 of the needle 54 and through the open slots 108, 112 of the jaw members 44a, 44b to mechanically decouple the laparoscopic suture passer 14 from the suture 34 (see FIG. 29O).

Figure 29P:
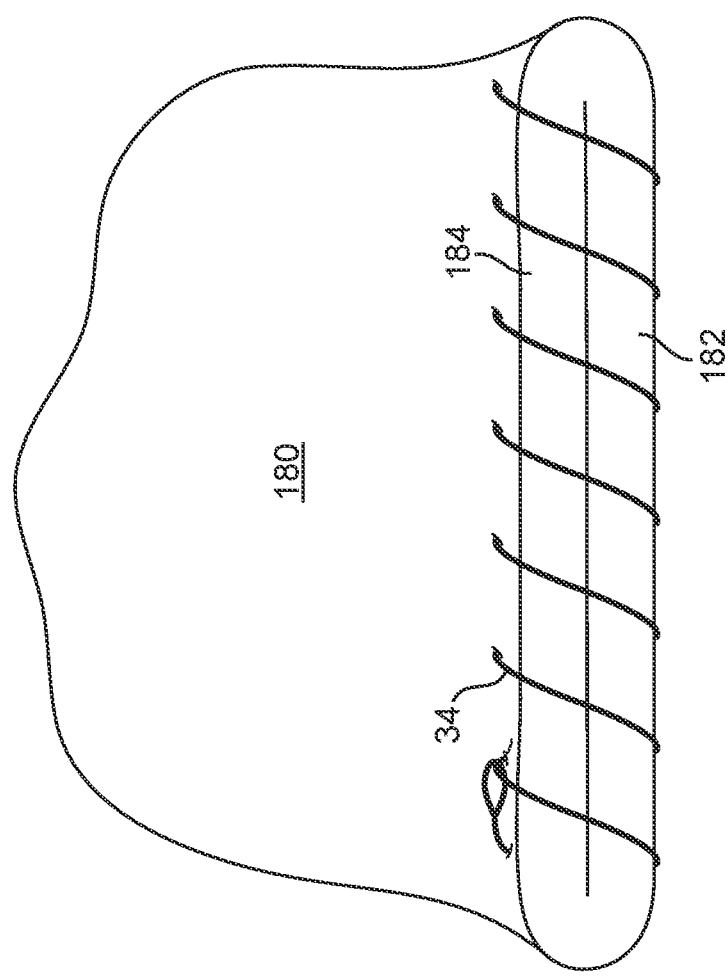

Once the vaginal cuff 180 is completely stitched (step 220) (see FIG. 29P), the needle 54 is hinged from the deployed position to the retracted via manipulation of the slider mechanism 60 (shown in FIG. 1) (step 222), the jaw members 44a, 44b of the laparoscopic suture passer 14 are displaced towards each other to the closed position via manipulation of the finger piece 50 (shown in FIG. 1) (step 224), and the laparoscopic suture passer 14 removed from the insufflated abdomen of the patient via the first laparoscopic port (step 226). The laparoscopic suture grasper 12, while the jaw members 24a, 24b are in the closed position, is removed from the insufflated abdomen of the patient via the second laparoscopic port (step 228). It should be appreciated that laparoscopic grasping instrument 12 may be removed from the insufflated abdomen of the patient before or after the removal of the laparoscopic suture passer 14.

Although particular embodiments of the disclosed inventions have been shown and described herein, it will be understood by those skilled in the art that they are not intended to limit the present inventions, and it will be obvious to those skilled in the art that various changes and modifications may be made (e.g., the dimensions of various parts) without departing from the scope of the disclosed inventions, which is to be defined only by the following claims and their equivalents. The specification and drawings are, accordingly, to be regarded in an illustrative rather than restrictive sense. The various embodiments of the disclosed inventions shown and described herein are intended to cover alternatives, modifications, and equivalents of the disclosed inventions, which may be included within the scope of the appended claims.

What is claimed is:

1. A laparoscopic suture passer, comprising:
an elongated shaft;
a jaw assembly coupled to a distal end of the elongated shaft, the jaw assembly comprising first and second jaw members hingedly associated with each other, the jaw members configured for being alternately displaced relative to each other between an open position and a closed position;
a hollow needle having a blunt end and a sharp end opposite the blunt end, the blunt end of the hollow needle hingedly coupled to the first jaw member for being alternately hinged between a retracted position when the hollow needle is stowed in the first jaw member, and a deployed position when the hollow needle extends away from the first jaw member; and
a linkage assembly extending along the elongated shaft, the linkage assembly comprising a connector extending through a through-hole formed in the blunt end of the needle and being coupled to the blunt end of the needle, wherein the hollow needle is configured for being hinged from the retracted position to the deployed position in response to actuation of the linkage assembly.

2. The laparoscopic suture passer of claim 1, wherein the needle is hollow.

3. The laparoscopic suture passer of claim 2, wherein the blunt end of the needle is funnel-shaped, the funnel-shaped end of the hollow needle having a base and a neck, wherein the base of the funnel-shaped end of the hollow needle narrows to the neck of the funnel-shaped end of the hollow needle towards the direction of the sharp end of the hollow needle, such that the funnel-shaped end of the hollow needle facilitates axial threading of a suture through the slotted bore of the hollow needle when the suture is inserted into the base of the funnel-shaped end of the hollow needle.

4. The laparoscopic suture passer of claim 2, wherein the hollow needle comprises a slotted bore extending along the entire length thereof.

5. The laparoscopic suture passer of claim 4, wherein each of the jaw members has a cleaved distal tip that defines an open slot therethrough when the jaw members are in the closed position, the sharp end of the deployed needle is configured for passing through the cleaved distal tip of the second jaw member as the jaw members are displaced relative to each other from the open position to the closed position, and the respective open slots in the jaw members are in communication with the slot of the hollow needle, such that a suture may be laterally removed distally from the slotted bore of the hollow needle and out of the open slots when the jaw members are in any position between the closed position and the open position, thereby decoupling the suture from the laparoscopic suture passer without cutting the suture.

6. The laparoscopic suture passer of claim 1, wherein the connector is coupled to the blunt end of the needle via a pin.

\* \* \* \* \*